United States Patent [19]

Lam et al.

[11] Patent Number: 5,686,282
[45] Date of Patent: Nov. 11, 1997

[54] DNA ENCODING THE PSEUDOMONAS FLUORESCENS SENSOR/KINASE ELEMENT, LEMA, AND ITS USE IN ACTIVATING GENE EXPRESSION

[75] Inventors: Stephen T. Lam, Raleigh; Thomas D. Gaffney, Chapel Hill, both of N.C.

[73] Assignee: Novartis Finance Corporation, New York, N.Y.

[21] Appl. No.: 459,701

[22] Filed: Jun. 2, 1995

Related U.S. Application Data

[60] Division of Ser. No. 287,442, Aug. 8, 1994, Pat. No. 5,670,350, which is a continuation-in-part of Ser. No. 258,261, Jun. 8, 1994, Pat. No. 5,639,949, which is a continuation-in-part of Ser. No. 87,636, Jul. 1, 1993, abandoned, which is a continuation-in-part of Ser. No. 908,284, Jul. 2, 1992, abandoned, which is a continuation-in-part of Ser. No. 570,184, Aug. 20, 1990, abandoned.

[51] Int. Cl.$^6$ .................. C12N 15/00; C12N 15/31; C12N 15/63; C12N 15/78

[52] U.S. Cl. .................. 435/172.3; 435/252.34; 435/320.1; 935/9; 935/27; 935/29; 935/39; 935/64; 935/72; 536/23.7

[58] Field of Search .................. 435/69.1, 252.3, 435/252.34, 320.1, 71.3, 172.3; 424/405, 43.7; 536/23.7

[56] References Cited

U.S. PATENT DOCUMENTS

| | | | |
|---|---|---|---|
| 4,306,027 | 12/1981 | Alexander et al. | 435/252.2 |
| 4,456,684 | 6/1984 | Weller et al. | 435/34 |
| 4,652,639 | 3/1987 | Stabinsky | 435/91.52 |
| 4,695,455 | 9/1987 | Barnes | 424/93.2 |
| 4,729,951 | 3/1988 | Forenczy et al. | 435/80 |
| 4,798,723 | 1/1989 | Dart et al. | 424/93.47 |
| 4,812,512 | 3/1989 | Berestein et al. | 424/417 |
| 4,880,745 | 11/1989 | Kijima et al. | 435/93.47 |
| 4,948,413 | 8/1990 | Maekawa et al. | 540/117 |
| 4,952,496 | 8/1990 | Studier et al. | 435/91.41 |
| 4,970,147 | 11/1990 | Huala et al. | 435/69.1 |
| 4,975,277 | 12/1990 | Janisiewicz et al. | 424/93.47 |
| 4,994,495 | 2/1991 | Clough et al. | 514/514 |
| 5,008,276 | 4/1991 | Clough et al. | 514/335 |
| 5,041,290 | 8/1991 | Gindrat et al. | 424/93.5 |
| 5,049,379 | 9/1991 | Handelsmon et al. | 424/115 |
| 5,059,605 | 10/1991 | Clough et al. | 514/269 |
| 5,068,105 | 11/1991 | Lewis et al. | 424/93.3 |
| 5,279,951 | 1/1994 | Terasawa et al. | 435/172.3 |

FOREIGN PATENT DOCUMENTS

| | | |
|---|---|---|
| 0414404 | 2/1991 | European Pat. Off. . |
| 0471564 | 2/1992 | European Pat. Off. . |
| 89-09264 | 12/1989 | WIPO . |
| WO/9105475 | 5/1991 | WIPO . |
| 9208355 | 5/1992 | WIPO . |

OTHER PUBLICATIONS

Fortkamp, E., et al., DNA, vol. 5, "Cloning and expression in *Escherichia coli* of a synthetic DNA for hirudin, the blood coagulation inhibitor in the leech", pp. 511–517. 1986.

Gutterson, N. I., et al., Journal of Bacteriology, vol. 165, "Molecular cloning of genetic determinants for inhibition of fungal growth by a flourescent pseudomonad", pp. 696–703 1986.

Albright, L. M., et al., Annual Review of Genetics, vol. 23, "Prokaryotic signal transduction mediated by sensor and regulator protein pairs", pp. 311–336. 1989.

(List continued on next page.)

*Primary Examiner*—Robert A. Wax
*Assistant Examiner*—William W. Moore
*Attorney, Agent, or Firm*—J. Timothy Meigs

[57] ABSTRACT

Gene activating sequences which activate the expression of other bacterial genes, which are latent or expressed at low levels, are provided. The gene activating sequences confer the ability to produce several metabolites and may be transferred to bacterial strains. The transformed biocontrol agents are active to inhibit the growth of the fungal pathogens.

12 Claims, 4 Drawing Sheets

| Clones of the second genetic region | Ability to complement CGP 21 |
|---|---|
| pCIB 146  R1 — H — R1 B — B B — R1 | + |
| R1 — H — R1 | − |
| R1 B — B B — R1 | − |
| R1 — H — R1 B — B — R1 | + |
| pCIB 168  H — R1 B | + |

OTHER PUBLICATIONS

Deretic, V., et al., Journal of Bacteriology, vol. 171, "Control of mucoidy in *Pseudomonas aeruginosa*: Transcriptional regulation of algR and identification of the second regulatory gene, algQ", pp. 3680–3688 1989.

Stock, J. B., et al., Microbiological Reviews, vol. 53, "Protein phosphorylation and regulation of adaptive responses in bacteria", pp. 450–490 1989.

Stout, V., et al., Journal of Bacteriology, vol. 172, "RcsB and RcsC: A two–component regulator of capsule synthesis in *Escherichia coli*", pp. 659–669 1990.

Bourret, R. B., et al., Annual Review of Biochemistry, vol. 60, "Signal transduction pathways involving protein phosphorylation in prokaryotes", pp. 401–441 1991.

Arico, B., et al., Molecular Microbiology, vol. 5, "Structural and genetic analysis of the bvg locus in Bordetella species", pp. 2481-2491 1991.

Laville, J., et al., Proceedings of the National Academy of Sciences, USA, vol. 89, "Global control in Pseudomonas fluorescens mediating antibiotic synthesis and suppression of black root rot of tobacco", pp. 1562–1566 1992.

Hrabak, E. M., et al., Journal of Bacteriology, vol. 174, "The lemA gene required for pathogenicity of Pseudomonas syringae pv. syringae on bean is a member of two–component regulators", pp. 3011–3020 1992.

Nagasawa, S., et al., Molecular Microbiology, vol. 6, "A novel sensor–regulator protein that belongs to the homologous family of signal transduction proteins involved in adaptive responses in Escherichia coil", pp. 799–807 1992.

Baker et al., "Examples of Biological Control", *Biological Control of Plant Pathogens*, pp. 61–106 (American Phytopathological Society, St. Paul, Minn. 1982).

Brisbane et al., *Soil Biol. Biochem*, 21(8): 1019–1026 (1989).

Brisbane, P.G., et al., 1987, *Antimicrobiol. Agents and Chemotherapy*, 31(12): 1967–1971.

Clarke et at., "Expression of the argF Gene of *Pseudomonas aeruginosa* in *Pseudomonas aeruginosa, Pseudomonas putida,* and *Escherichia coli,*" *J. Bacteriol.* 154:508–512 (1983).

Cook et al., "The role of bacteria in the biological control of *Gaeumannomyces graminis* by suppressive soils", *Soil Biol. Biochem.*, 8:269–273 (1976).

Ding et al., "Orientation and expression of the cloned hemnolysis gene of *Pseudomonas aeruginosa*", *Gene*, 33(3): 313–321 (1985).

Ditta et al., "Broad host range DNA cloning system for Gram–negative bacteria: Construction of a gene bank of *Rhizobium meliloti*", *Proc. Natl. Acad. Sci. USA*, 77:7347–7351 (1980).

Gamnbello et al., "Cloning and Characterization of the *Pseudomonas aeruginosa IasR* Gene, a Transcriptional Activator of Elastase Expression", *J. Bacteriology*, 173(9): 3000–3009 (1991).

Gurusiddaiah et al., *Antimicrobiol. Agents and Chemotherapy*, 79(3): 488–495. (1986).

Hamdan et al., "Relative Importance of Fluorescent Siderophores and Other Factors in Biological Control of *Gaeumannomyces graminis* var. tritici by *Pseudomonas fluorescens* 2–79 and M4–80R", *Applied and Environ. Microbiol.*, 57:3270–3277 (1991).

Horn et al., "Autogenous Regulation and Kinetics of Induction of *Pseudomonas aeruginosa* recA Transcription as Analyzed with Operon Fusions", *J. Bacteriology*, 170(10): 4699–4705 (1988).

Howell et al, "Control of *Rhizoctonia solani*, on Cotton Seedlings with *Pseudomonas fluorescens* and With an Antibiotic Produced by the Bacterium", *Phytopathology*, 69(5): 480–482 (1979).

Howell et al., *Can. J. Microbiol.*, 29:321–324 (1983).

Howell et al., "Suppression of *Pythiurm ultimum*–Induced Damping–Off of Cotton Seedlings by *Pseudomonas fluorescens* and its Antibiotic, Pyoluteorin", *Phytopathology*, 70:712–715 (1980).

Howie, W., et al., "Directed Enhancement of Biocontrol in Pseudomonas by Constitutive; Antibiotic Biosynthesis", *Phytopathology*, 79(10): 1160 (1989), Abstract 201, 1989 Annual Meeting, 8th American Phytopathological Society.

Inouye et al., "Molecular Cloningof Regulatory Gene xylR and Operator–Promoter Regions of the xylABC and xylDEGF Operons of the TOL Plasmid", *J. Bacteriology*, 155(3): 1192–1199 (1983).

James et al., "Multiple Antibiotics Produced by *Pseudomonas fluorescens* HV37a and Their Differential Regulation by Glucose", Applied and Environmental *Microbology*, 52(5): 1183–1189 (1986).

Jeenes et al., "Expression of biosynthetic genes from *Pseudomonas aeruginosa* and *Escherichia coli* in the heterologous host", *Mol. Gen. Genet.*, 203:421–429 (1986).

Kaphammer et al., "Cloning and Characterization of tfdS, the Repressoro–Activator Gene of tfdB, from the 2,4–Dichlompheoroxyacetic Acid Catabolic Plasmid pJP4", *J. Bacteriology*, 172(10): 5856–5862 (1990).

Keel et al., *Symbiosis*, 9(1–3): 327–341 (1990).

Klee et al., "Control of Ethylene Synthesis by Expression of a Bacterial Enzyme in Transgenic Tomato Plants", *The Plant Cell*, 3:1187–1193 (1991).

Kloepper et al., "Relationship of in vitro antibiosis if plant growth–promoting rhizobacteria to plant growth and the displacement of root microflora", *Phytopathology*, 71: 1020–1024 (1981).

Kraus, J., et al., "TN5 Insertion Mutants of Pseudomonas Fluorescens PF5 Altered in Production of the Antibiotics of Pyrrolnitrin and Pyoluteorin", *Phytopathology*, 79(8):910, Abstract for Annual Meeting, Pacific Division, The American Phytopathological Society (1989).

Kroos et al., "Construction of Tn5 lac, a transposon that fuses lacZ expression to exogenous promoters, and its introduction onto *Myxococcus xanthus*", *PNAS USA*, 81:5816–5820) (1984).

Lievens et al., *Pesticide Science*, 27(2): 141–154 (1989).

Loper, "Role of Fluorescent Siderophore Production in Biological Control of *Pythium ultimum* by a *Pseudomonas fluorescens* Strain", *Phytopathology*, 78:166–171 (1988).

Mekalanos, "Environmental Signals Controlling Expression of Virulence Determinants In Bacteria:", *J. Bacteriology*, 174 (1): 1–7 (1992).

Mermod et al., "Vector for Regulated Expression of Cloned Genes in a Wide Range of Gram–Negative Bacteria", *J. Bacteriology*, 167(2): 447–454 (1986).

Mohr et al., *Molecular Microbiology*, 4(12): 2103–2110(1990).

Moolenaar et al., "Regulation of the *Escherichia coli* excision repair gene uvrC. Overlap between the uvrC structural gene and the region coding for a 24 kD protein", *Nucl. Acids Res.*, 15(10): 4273–4289 (1989).

Orlik–Eisel et al., "The cytotoxin of *Pseudomonas aeruginosa*: Cytotoxicity requires proteolytic activation", *Microbiology*, 153(6): 561–568 (1990).

Ramos et al., "Redesigning Metabolic Routes: Manipulation of TOL Plasmid Pathway for Catabolism of Alkylbenzoates", *Science*, 235(4788): 593–596 (1987).

Rothmel et al., "Functional Analysis of the *Pseudomonas putida* Regulatory Protein CatR: Transcriptional Studies and Determination of the CatR DNA–Binding Site by Hydroxy-l–Radical Footprinting", *J. Bacteriology*, 173(15): 4717–4724 (1991).

Schell, "Transcriptional control of the nah and sal hydrocarbon–degradation operons by the nahR gene product", *Gene*, 36(3): 301–309 (1985).

Scher et al., "Mechanism of Biological Control in a Fusarium–Suppressive Soil", *Phytopathology*, 70:412–417 (1980).

Schroth et al., *Science*, 216:1376–1381 (1982).

Spena et al., "The indoleacetic acid–lysine synthetase gene of *Pseudomonas syringae* subsp. savastanoi induces developmental alterations in transgenic tobacco and potato plants", *Mol. Gen. Genet.*, 227:205–212 (1991).

Starnbach et al., "The fliA (rpoF) gene of *Pseudomonas aeruginosa* encodes an alterntive sigma factor required for flagellin synthesis", *Molecular Microbiology*, 6(4): 459–469 (1992).

Tanaka et al., "Cloning and Chracterization of *Bacillus subtilis iep*, Which Has Positive and Negative Effects on Production of Extracellular Proteases", *J. Bacteriology*, 170(8):3593–3600 (1988).

Thomashow et al., "Role of a Phenazine Antibiotic from *Pseudomonas fluorescens* in Biological Control of *Gaeumannomyces graminis* var. tritici, *J. Bacteriology*", 170(8): 3499–3508 (1988).

Toder et al., "Pseudomonas aeruginosa LasA: a second elastase under the transcriptional control of lasR" *Molecular Microbiology*, 5(8): 2003–2010 (1991).

Weller et al., "Antibiotics: Evidence for their Operation and Sites Where They Might Be Produced", *Journal of Cellular Biochemistry*, Supplement 13A: 154, (1989) Abstract CB014.

Weller et al., "Suppression of take–all of wheat by seed treatment with fluorescent Pseudomonads", *Phytopathology*, 73:463–469 (1983).

Wolfframm et al., *FEBS Letter*, 238:325–328 (1988).

DNA ENCODING THE PSEUDOMONAS FLUORESCENS SENSOR/KINASE ELEMENT, LEMA, AND ITS USE IN ACTIVATING GENE EXPRESSION

This is a divisional application of Ser. No. 08/287,442, filed Aug. 8, 1994, now U.S. Pat. No. 5,670,350, issued on Sep. 23, 1997, which is a continuation-in-part of Ser. No. 08/258,261, filed Jun. 8, 1994, now U.S. Pat. No. 5,639,949, issued on Jun. 17, 1997, which is a continuation-in-part of Ser. No. 08/087,636, filed Jul. 1, 1993, now abandoned which is a continuation-in-part of Ser. No. 07/908,284, filed Jul. 2, 1992, now abandoned which is a continuation-in-part of Ser. No. 07/570,184, filed Aug. 20, 1990, now abandoned.

FIELD OF THE INVENTION

The present invention relates to the identification, isolation, cloning and use of genetic elements which contribute to the activation of genes in bacterial strains. More specifically, the invention relates to the identification of three classes of genetic elements which interact with each other in the activation of genes in bacteria. Manipulation of these types of elements, either separately or in combination, can be used to manipulate bacterial phenotype.

BACKGROUND OF THE INVENTION

It has been recognized that crops grown in some soils are naturally resistant to certain fungal pathogens. Furthermore, soils that are conducive to the development of these diseases can be rendered suppressive, or resistant, by the addition of small quantities of soil from a suppressive field. Scher et al. Phytopathology 70:421 (1980). Conversely, suppressive soils can be made conducive to fungal diseases by autoclaving, indicating that the factors responsible for disease control are biological. Subsequent research has demonstrated that root colonizing bacteria are responsible for this phenomenon known as biological disease control (BDC). Baker et at., *Biological control of plant pathogens*, (Freeman Press, San Francisco) (1974).

In many cases, the most efficient strains of biological disease controlling bacteria are fluorescent Pseudomonads. Weller et al., *Phytopathology*, 73:463–469 (1983). These bacteria have also been shown to promote plant growth in the absence of a specific fungal pathogen by the suppression of detrimental rhizosphere microflora present in most soils. Kloepper et al., *Phytopathology* 71: 1020–1024 (1981). Important plant pathogens that have been effectively controlled by seed inoculation with these bacteria include *Gaemannomyces gramminis*, the causative agent of take-all in wheat, Cook et al., *Soil Biol. Biochem* 8:269–273 (1976) and Pythium and Rhizoctonia, pathogens involved in damping off of cotton. Howell et al, *Phytopathology* 69:480–482 (1979). Rhizoctonia is a particularly problematic plant pathogen for several reasons. First, it is capable of infecting a wide range of crop plants. Second, there are no commercially available chemical fungicides that are effective in controlling the fungus. Because of these circumstances, an inhibitor against *R. solani* would be of substantial interest as a potential control for this pathogen.

Many biological disease controlling Pseudomonas strains produce antibiotics that inhibit the growth of fungal pathogens. Howell et al, *Phytopathology* 69:480–482 (1979); Howell et al. *Phytopathology* 70:712–715 (1980). These have been implicated in the control of fungal pathogens in the rhizosphere. Several past studies have focused on the effects of mutations that result in the inability of the disease control bacterium to synthesize these antibiotics. Kloepper et al., *Phytopathology* 71: 1020–1024 (1981); Howell et al., *Can. J. Microbial.* 29:321–324 (1983). In these cases, the ability of the organism to control the pathogen is reduced, but not eliminated. In particular, Howell et al., *Phytopathology* 69:480–482 (1979) discloses a strain of *Pseudomonas fluorescens* which was shown to produce an antibiotic substance that is antagonistic to *Rhizoctonia solani*.

In Baker et al., *Biological Control of Plant Pathogens*, (American Phytopathological Society, St. Paul, Minn.) (1982), pages 61–106, it is reported that an important factor in biological control is the ability of an organism to compete in a given environment. Thus, it is desirable to obtain mains of biocontrol agents which are effective to control the growth of fungal pathogens, such as *Rhizoctonia solani*, *Helminthosporium gramineae* and species of the genera Pythium and Fusarium and are able to aggressively compete with indigenous bacteria and microflora that exist in the rhizosphere of the plant. In order to achieve this objective, it is further desirable to obtain DNA sequences which are useful in conferring resistance to fungal pathogens which may be used to genetically engineer strains of biocontrol agents that combine the ability to control the growth of fungal pathogens with the ability to control other plant pathogens and/or the ability to aggressively compete in the rhizosphere.

Bacterial two-component regulatory systems have been extensively reviewed (e.g. Albright et al., *Annu. Rev. Genet.* 23:311–336 (1989); Bourret et al., Annu. Rev. Biochem. 60:401–441 (1991); Mekalanos, J. Bacteriol. 174:1–7 (1992)). In most instances, an environmental signal is received by a sensor protein component. Reception of the signal induces an autophosphorylation event and a change in the conformation of the sensor protein. In this new conformation, the sensor is capable of phosphorylating the amino-terminal portion of the activator protein component. This phosphorylation event is thought to alter the conformation of the activator protein such that the DNA binding module of its carboxy-terminal end is capable of interacting with the promoter regions of regulated genes within the network.

Laville et al., PNAS:USA 89:1562–1566 (1992) disclose the isolation from *Pseudomonas fluorescens* CHA0, an activator-component gene designated gacA which was required for the expression of genes involved in the synthesis of the antifungal secondary metabolites 2,4-diacetylphloroglucinol, cyanide, and pyoluteorin. The strain was indicated to be capable of suppressing black root rot of tobacco caused by the fungal pathogen *Thielaviopsis basicola*. Disruption of the gacA gene resulted in a mutant unable to synthesize any of these secondary metabolites and significantly reduced in its ability to suppress black root rot. Laville et al. concluded that the gacA gene was involved in regulation of secondary metabolism in *P. fluorescens* and inferred that extracellular secondary metabolites produced under gacA control are important for the biocontrol of black root rot. They noted the presence of a gene homologous to gacA in *E. coli* and cited preliminary evidence from hybridization experiments that a sequence similar to gacA exists in *Pseudomonas aeruginosa*.

Our data indicate that antifungal secondary metabolites are likely only a subset of factors under the regulatory control of the ORF 5 gene we have cloned from *Pseudomonas fluorescens*, since we have discovered that ORF 5, (gafA) also affects the production of hydrolytic enzymes such as chitinase and gelatinase which are involved in the catabolism of polymeric carbon sources. Laville et al. did not disclose or suggest that the gacA gene was involved in activation of latent genes by a transcriptional activator or suggest that an activator derived from one bacterial strain would induce expression of genes from a heterologous bacterium. To our knowledge, the present invention is the first to describe the unexpected finding that certain natural bacterial isolates carry undetected, latent genes which can be activated upon introduction of a bacterial transcription activator derived from a different organism (in this case, either upon introduction of a 2.0 kb XhoI fragment of *P. fluorescens* strain 915 DNA containing ORF 5 or upon introduction of a cloned *E. coli* gene homologous to ORF 5, gafA).

A number of sensory-component genes have been characterized from different microorganisms (for reviews see Bourret et al., 1991 and Stock et al., 1990). In one case the sensory component gene, referred to as lemA, was found to be required for the pathogenicity of *Pseudomonas syringae* (Hrabak et al., (1992) *J. Bacteriol.* 174:3011–3020. However, in contradiction to the data presented in this application, Hrabak et al. proposed that lemA alone may perform sensory and regulatory functions. Our experiments characterize a member of the same gene family cloned from *Pseudomonas fluorescens* and reveal that it plays a crucial role in gene activation by interacting with the global regulatory element gafA.

In *Escherichia coli*, it has been demonstrated that an alternate sigma factor designated rpoS is required for the transcription of a large set of genes which are preferentially expressed during stationary phase conditions (i.e. conditions of nutrient stress) (Siegele and Kolter, J. Bacteriol. 174:345–348 (1992); Hengge-Aronis, Cell 72:165–168 (1993)). The present invention provides a characterization of a member of the rpoS gene family cloned from *Pseudomonas fluorescens* and reveals its crucial role in gene activation.

SUMMARY OF THE INVENTION

Accordingly, it is one object of the present invention to provide DNA sequences which are useful in activating genes in bacterial strains.

It is another object of the present invention to provide genes that can be used to improve the biocontrol capabilities of strains of bacteria used for biocontrol.

It is one feature of the present invention that DNA sequences and genes are provided that activate genes in bacterial strains.

It is a further feature of the present invention that modified DNA sequences and genes be provided which encode modified proteins, which enhance the activation of genes in bacterial strains. Such modifications may improve the efficacy of regulatory genes.

It is an advantage of the present invention that biocontrol agents may be produced which are able to inhibit a broad spectrum of plant pathogens.

It is another advantage of the present invention that biocontrol agents may be produced which are able to aggressively compete in the plant rhizosphere, which biocontrol agents contain a DNA sequence that activates genes in the bacterial biocontrol agent.

According to the present invention, the above objectives may be carried out by the isolation and use of genetic elements or gene activating sequences that are able to activate genes that are not normally mined on in bacterial strains. The isolation of these gene activating sequences is important for several reasons. First, the activated strains produce substances, such as pyrrolnitrin and chitinase, which are able to inhibit plant pathogens, particularly fungal pathogens, such as *Rhizoctonia solani, Helminthosporium gramineae* and species of the genera Pythium and Fusarium. Therefore, use of bacterial strains transformed with the ORF 5-type, lemA-type, or rpoS-type genetic element (or combinations of these elements) provides an environmentally safe and effective method of control of these pathogens.

In addition, these gene activating sequences can be transferred to other bacterial strains, especially pseudomonad strains, that otherwise are not effective biocontrol agents for *R. solani* and thereby transform them into effective biocontrol strains. The use of the gene activating sequences to improve the biocontrol capabilities of other strains of rhizosphere biocontrol strains is also pan of the present invention. For example, U.S. Pat. No. 4,456,684, (Weller et al.) discloses that take-all, a disease of wheat caused by the fungus *Gaemannomyces gramminis*, can be controlled in some cases by the application of bacteria inhibitory to this pathogen to wheat seeds prior to planting. However, where the growth of *G. gramminis* is effectively under control, *R. solani* may become a growing problem pathogen of wheat. The gene activating sequence for activation of genes which are effective against *R. solani* could be introduced into the biocontrol strains currently used to protect wheat from take-all to extend their range of effectiveness to include *R. solani*.

The present invention comprises an isolated DNA sequence consisting essentially of the 2 kb fragment deposited as pCIB 137, or of the ORF 5 sequence shown in SEQUENCE ID No. 1. These DNA sequences are capable of activating latent gene activity in a bacterial strain. Thus, the present invention also comprises methods of activating latent gene activity in a host bacterial strain comprising introducing the DNA sequence into the genome of a host bacterial strain. In preferred embodiments of the invention, the host bacterial strain may be a pseudomonad, particularly strains of the species *Pseudomonas fluorescens*.

The present invention further comprises recombinant DNA sequences in which a bacterial regulatory element is operably linked to the DNA sequence of SEQUENCE ID No. 1. The bacterial regulatory element may be a promoter from a gene isolated from Pseudomonas, Bacillus, or *E. coli*. In one embodiment of the present invention, the bacterial regulatory element is the native promoter of ORF 5. The bacterial regulatory element may be from a gene which is homologous or heterologous to the host bacterial strain.

The present invention also includes methods of activating latent gene activity in a host bacterial strain by transforming the host bacterial strain with the recombinant DNA sequences of the present invention. In a particular embodiment of the present invention, the transformed host bacterial strain is rendered active against fungal pathogens, such as *Rhizoctonia solani, Helminthosporium gramineae* and species of the genera Pythium and Fusarium.

The present invention further comprises isolated DNA sequences encoding the lemA gene. These sequences are capable of restoring the production of hydrolytic enzymes such as chitinase and gelatinase and the production of antifungal secondary metabolites such as pyrrolnitrin and cyanide in some mutants lacking these functions. The invention further comprises recombinant DNA sequences in which a bacterial regulatory element is operably linked to the DNA coding sequence of lemA. The bacterial regulatory element may be a promoter from a gene isolated from Pseudomonas, Bacillus, or *E. coli*. In one embodiment of the present invention, the bacterial regulatory element is the native promoter of lemA. The bacterial regulatory element may also be from a gene which is homologous or heterologous to the host bacterial strain.

The present invention further comprises isolated DNA sequences encoding the rpoS gene. These sequences are capable of restoring the production of hydrolytic enzymes such as chitinase and gelatinase and the production of antifungal secondary metabolites such as pyrrolnitrin and cyanide in some mutants lacking these functions. The invention further comprises recombinant DNA sequences in which a bacterial regulatory element is operably linked to the DNA coding sequence of rpoS. The bacterial regulatory element may be a promoter from a gene isolated from Pseudomonas, Bacillus, or E. coli. In one embodiment of the present invention, the bacterial regulatory element is the native promoter of rpoS. The bacterial regulatory element may also be from a gene which is homologous or heterologous to the host bacterial strain.

The present invention also includes methods of activating genes whose expression is regulated by Gene Activating sequences by introducing the recombinant Gene Activating sequences of the present invention, alone or in combination, into the host bacterial strain. Preferred for use as Gene Activating Sequences in this method are the gafA, lemA and rpoS genes, and any combination thereof. In a particular embodiment of the present invention, the transformed host bacterial strain is rendered active against fungal pathogens, such as Rhizoctonia solani, Helminthosporium gramineae and species of the genera Pythium and Fusarium.

The present invention also includes a method for the isolation of biosynthetic genes for anti-pathogenic substances which utilizes the Gene Activating Sequences which control their expression.

Examples of the gene activating sequences of the present invention have been deposited. Accordingly, the gene activating sequence includes the deposited DNA sequence as well as fragments thereof. By fragments is intended a DNA sequence which is capable of functioning as a gene activating sequence.

DEFINITIONS

As used in the present application, the following terms have the meaning set out below:

Antipathogenic Substance (APS): A substance which requires one or more nonendogenous enzymatic activities foreign to a plant to be produced in a host where it does not naturally occur, which substance has a deleterious effect on the multiplication or growth of a pathogen (i.e. pathogen). By "nonendogenous enzymatic activities" is meant enzymatic activities that do not naturally occur in the host where the antipathogenic substance does not naturally occur. A pathogen may be a fungus, bacteria, nematode, virus, viroid, insect or combination thereof, and may be the direct or indirect causal agent of disease in the host organism. An antipathogenic substance can prevent the multiplication or growth of a phytopathogen or can kill a phytopathogen. An antipathogenic substance may be synthesized from a substrate which naturally occurs in the host. Alternatively, an antipathogenic substance may be synthesized from a substrate that is provided to the host along with the necessary nonendogenous enzymatic activities. An antipathogenic substance may be a carbohydrate containing antibiotic, a peptide antibiotic, a heterocyclic antibiotic containing nitrogen, a heterocyclic antibiotic containing oxygen, a heterocyclic antibiotic containing nitrogen and oxygen, a polyketide, a macrocyclic lactone, and a quinone. Antipathogenic substance is abbreviated as "APS" throughout the text of this application.

Promoter or Regulator DNA sequence: An untranslated DNA sequence which assists in, enhances, or otherwise affects the transcription, translation or expression of an associated structural DNA sequence which codes for a protein or other DNA product. The promoter DNA sequence is usually located at the 5' end of a translated DNA sequence, typically between 20 and 100 nucleotides to the 5' end of the starting site for translation.

Structural or Coding DNA sequence: A DNA sequence that is translated or transcribed in an organism to produce an RNA, a protein or other DNA product.

Associated with/operably linked: Two DNA sequences which are "associated" or "operably linked" are related physically or functionally. For example, a promoter or regulator DNA sequence is said to be "associated with" a DNA sequence that codes for an RNA or a protein if the two sequences are operably linked, or situated such that the regulator DNA sequence will affect the expression level of the coding or structural DNA sequence.

Derived from: A first DNA sequence or fragment is said to be "derived from" a second DNA sequence or fragment if the former is physically isolated from the latter, or if the former is isolated based on sequence homology by using part or all of the latter as a probe for isolation. The degree of sequence homology is sufficient to allow specific hybridisation of the probe to the first DNA sequence and is 50% or greater, preferably greater than 60% and most preferably greater than 75%.

Homologous: A DNA sequence is said to be "homologous" to a host organism, such as a bacterial strain, if that DNA sequence was originally isolated from, or naturally originates in, the genome of an organism of similar biological classification as the host organism. For example, where a host organism to be transformed is of the species Pseudomonas fluorescens, a DNA sequence is homologous if it originates from a pseudomonad strain, particularly from a strain of the genus Pseudomonas, especially the species Pseudomonas fluorescens. The term "heterologous" is used to indicate a recombinant DNA sequence in which the promoter or regulator DNA sequence and the associated DNA sequence are isolated from organisms of different biological classification.

Chimeric construct/chimeric DNA sequence: A recombinant DNA sequence in which a regulator or promoter DNA sequence is associated with, or operably linked to, a DNA sequence that codes for an mRNA or which is expressed as a protein, such that the regulator DNA sequence is able to regulate transcription or expression of the associated DNA sequence. The regulator DNA sequence of the chimeric construct is not normally operably linked to the associated DNA sequence as found in nature.

Genome: The term "genome" refers to the entire native genetic content of an organism. The genome of bacterial organisms may include both the chromosomal and plasmid DNA content of an organism.

Gene activating sequences: Sequences which, when transformed into a host, have the ability to turn on other genes which are not expressed (i.e. latent) or expressed at low levels in the naturally occurring state of the host. These sequences typically encode proteins which play a role in the pathways which regulate gene expression. These sequences include, but are not limited to, the gafA, lemA and rpoS genes.

DETAILED DESCRIPTION OF THE INVENTION

Figure 1:
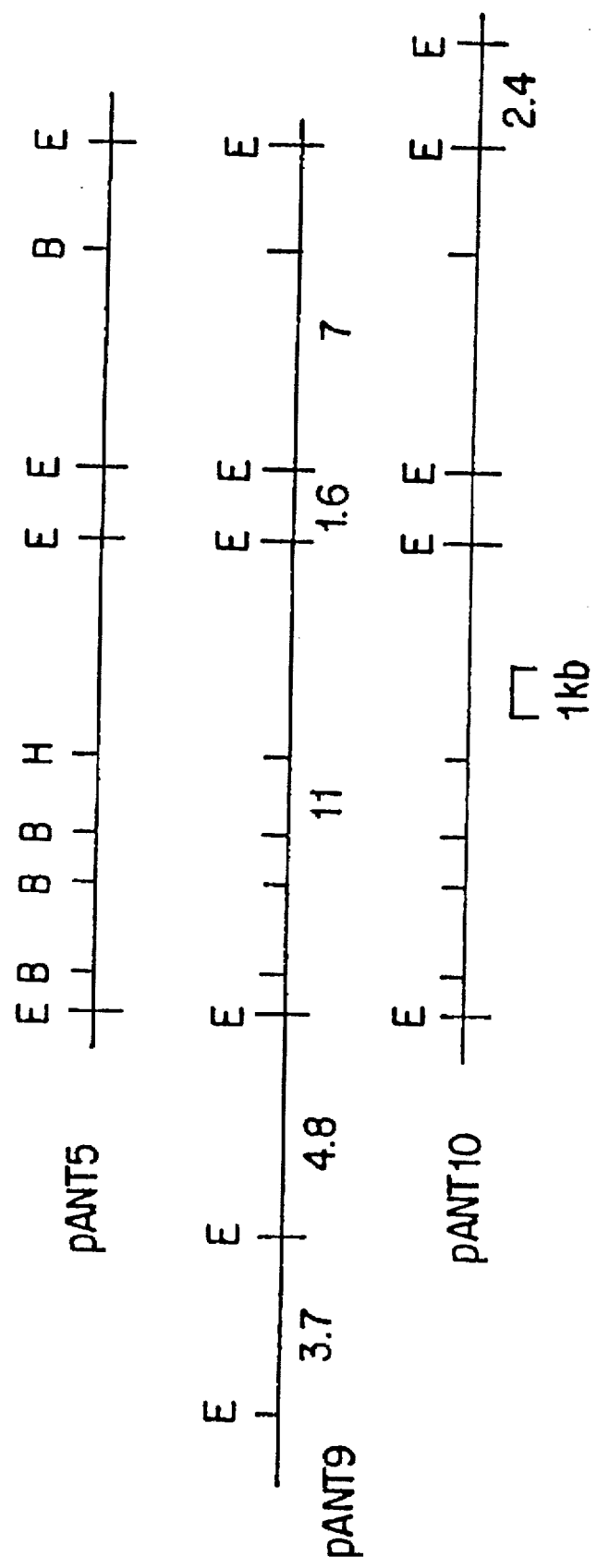
FIG. 1: This figure shows restriction maps of three cosmid clones, pANT5, pANT9 and pANT10, that were found to complement the ANT⁻ phenotype of mutant 2-1. In this figure, 'B' indicates a BamHI restriction site; 'E' an EcoRI restriction site; and 'H' a HindIII restriction site.

*Pseudomonas fluorescens* strain 915 was isolated from the roots of a cotton plant grown in a Texas cotton field and was identified as an effective biocontrol strain of *Pythium ultimum*- and *Rhizoctonia solani*-induced damping off of cotton. We have determined that certain mutant derivatives of the bacterial biological control strain *Pseudomonas fluorescens* strain 915 are deficient or altered in a variety of functions. Such pleiotropic mutants can be isolated following mutagenesis techniques known to those skilled in the art (e.g. nitrosoguanidine mutagenesis, transposon mutagenesis) or can arise spontaneously. One such mutant, obtained after mutagenesis with the chemical mutagen nitrosoguanidine was designated mutant 2-1. Seven further mutants were identified by introducing the transposon TnCIB116 into strain 915. These mutants Can be identified on the basis of their inability to inhibit in vitro the growth of the phytopathogenic fungus *Rhizoctonia solani*. They also fail to synthesize the antifungal metabolite pyrrolnitrin, and no longer produce cyanide or the enzyme chitinase, each of which has the potential to inhibit fungal growth (Voisard et al., EMBO J. 8:351–358 (1989); Jones et al., EMBO J. 5:467–473 (1986)). The mutants' production of an enzyme with gelatinase activity is significantly reduced, and they have an altered colony morphology. A summary comparing the characteristics of the pleiotropic mutants with the corresponding characteristics of wild-type *P. fluorescens* strain 915 is presented in Table 1.

TABLE 1

| Characteristics | *P. fluorescens* strain 915 | Pleiotropic mutants |
| --- | --- | --- |
| Pyrrolnitrin | + | − |
| Cyanide | + | − |
| Chitinase | + | − |
| Gelatinase | + | reduced |
| Colony morphology | circular, entire, convex and opaque | circular, undulate, flat and translucent |
| Inhibition of *Rhizoctonia solani* | + | − |

A total of eight pleiotropic mutants was identified. These all have the phenotype described in Table 1 above and fall into two distinct genetic classes, those which can be restored to 915-phenotype by introduction of the gafA gene (see A below) and those which can be restored to 915-phenotype by the introduction of the lemA gene (see B below).

A. Mutant Complementation with the gafA gene

An 11 kilobase EcoRI restriction fragment (referred to as fragment "E11") of *P. fluorescens* strain 915 was identified on the basis of its ability to restore antibiosis to a mutant, designated strain 2-1, and two further mutants (derived from insertion mutagenesis) which were otherwise incapable of inhibiting the growth of the phytopathogen *Rhizoctonia solani* in vitro or in greenhouse biological control assays. The 11 kilobase EcoRI restriction fragment (fragment E11) of *P. fluorescens* strain 915, and a 2.0 kb XhoI subclone of this fragment containing gafA (ORF 5), each restored all of the lost or altered functions listed in Table 1 when introduced by conjugation into one class of pleiotropic mutants derived from strain 915. Introduction of fragment E11 or the 2.0 kb XhoI subclone into the *P. fluorescens* strains 914 and 922 unexpectedly activate the expression of latent genes involved in the synthesis of pyrrolnitrin, cyanide, and chitinase, and in the case of *P. fluorescens* strain 914, cause an alteration in colony morphology on minimal medium from large, circular, flat, translucent, with undulate edge to small, circular, convex, opaque white, with entire edge. Accompanying these phenotypic changes associated with the introduction of fragment E11 or the 2.0 kb XhoI subclone is the conversion of *P. fluorescens* strains 914 and 922 to effective biocontrol strains with activity against the phytopathogen *Rhizoctonia solani*. We have also demonstrated that introduction of an *Escherichia coli* gene homologous to ORF 5 (gafA) into *P. fluorescens* strain 914 activates the expression of genes involved in the synthesis of cyanide, chitinase, and pyrrolnitrin. This result indicates that genes of the gafA class are sufficient for the activation of latent genes in heterologous bacterial strains.

Figure 3:
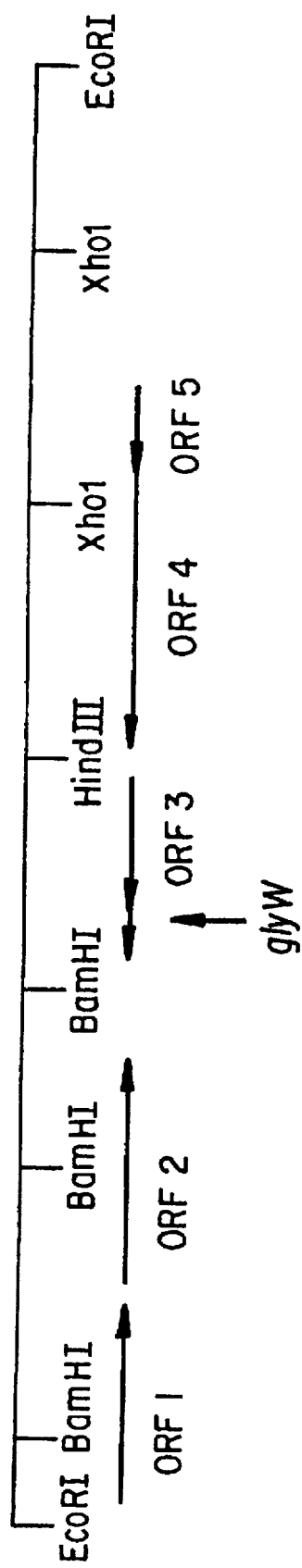
FIG. 3: This figure indicates the organization of the E11 fragment. The figure indicates the location of five identified open reading frames (ORF) and restriction sites for various enzymes.

DNA sequence analysis of fragment E11 has, to date, allowed identification of five open reading flames, as well as a tRNA gene (glyW). The organization of these open reading flames within fragment E11 is depicted in FIG. 3. The first potential gene regulation element we identified is ORF 2, which shared homology with numerous sensor components of bacterial two-component regulatory systems (reviewed in Albright et al., Annu. Rev. Genet. 23:311–336 (1989)). We determined that the organization of glyW, ORF 3 (which has homology to the *Escherichia coli* gene pgsA) and ORF 4 (which has homology to the *E. coli* gene uvrC) is identical to the gene organization found near map position 42 of the *E. coli* genome. In *E. coli*, at a position equivalent to ORF 5 (gafA), exists a putative transcriptional activator gene of unknown function (Moolenaar et al., Nucl. Acids Res. 15:4273–4289 (1987)). ORF 5 (gafA) exhibits homology to this putative activator gene. Furthermore, comparison of the fragment E11 sequence with DNA sequences contained in the Genbank database reveals that ORF 5 has substantial homology to a proposed transcriptional activator gene isolated from *Pseudomonas fluorescens* CHA0 by Laville et al., Proc. Natl. Acad. Sci. USA 89:1562–1566 (1992). Thus, two of the open reading flames, ORF 2 and ORF 5, share significant homology with numerous sensor and activator components, respectively, of bacterial two-component regulatory systems (reviewed in Albright et al., Annu. Rev. Genet. 23:311–336 (1989)).

Subcloning experiments are performed with fragment E11 with the aim of determining whether the gene(s) responsible for restoring lost functions to the pleiotropic mutants and for activating latent activities in heterologous Pseudomonas strains could be isolated on a smaller restriction fragment. A 2.0 kb XhoI subclone coming ORF 5 is prepared, as is a 3.7 kb EcoRI-XbaI subclone containing ORF1 and ORF 2. The 2.0 kb XhoI subclone is sufficient to restore the lost functions in the class of pleiotropic mutants originally complemented by fragment E11 and activated the expression of latent genes in *P. fluorescens* strains 914 and 922. The 3.7 kb EcoRI-XbaI subclone had no measurable effect. Furthermore, when the gafA gene was cloned from the strain 914, transferred to plasmid pLAFR3 and reintroduced into strain 914 the latent genes are activated indicating that strain 914 does contain a gafA gene capable of functioning, but that the expression of the gafA gene in strain 914 is presumably not at levels high enough to activate the latent genes.

To determine whether transcriptional activators of the gafA class are generally capable of activating the expression of latent genes in heterologous bacterial strains, we cloned the putative transcriptional activator gene described by Moolenar et al. and introduced it into P. fluorescens strain 914. The E. coli gene, which encodes a protein which is approximately 60% homologous to that encoded by gafA, activated the expression of genes involved in the production of cyanide, chitinase, and pyrrolnitrin in P. fluorescens strain 914.

It is an aspect of the present invention that improved biological control strains can be identified following the introduction of transcriptional activators of the gafA class into a variety of environmental isolates. This approach represents a method for the identification of potentially effective biocontrol strains which would otherwise not be selected by any of the screening methods currently available.

Those skilled in the art will also be aware that it will be possible to improve a biological control strain by placing additional genes under the control of transcriptional activators of the gafA class. This can be accomplished by identifying the gafA-responsive promoter element(s) and operably linking the desired gene or genes to such element(s) before introducing such genes into the desired strain.

In one embodiment of the present invention, recombinant DNA sequences are obtained which comprise an approximately 2 Kb DNA sequence consisting essentially of the DNA sequence of gafA. This DNA sequence demonstrates pleiotropic effects of activating latent gene activity or increasing the efficacy of other genes. Among the pleiotropic effects of the gafA DNA sequence are the increased ability to inhibit the growth of fungal pathogens, such as Rhizoctonia solani, Helminthosporium gramineae and species of the genera Pythium and Fusarium. This DNA sequence may be derived from bacterial strains which are effective biocontrol agents against Rhizoctonia. Preferably the DNA sequence may be derived from the done pANT5, which was isolated from a strain of Pseudomonas fluorescens. More preferably, the DNA sequence may comprise the approximately 11 kb E11 fragment of pANT5. In particular embodiments of the invention, the DNA sequence consists essentially of the approximately 2 kb fragment, or the DNA sequence of SEQUENCE ID No. 1. The clone pANT5 has been deposited with ATCC and has been designated ATCC accession number 40868. A plasmid containing the 11 kb E11 fragment of pANT5 has been deposited with ATCC and has been designated ATCC accession number 40869. The approximately 2 kb ORF 5 DNA sequence may be obtained from the E11 fragment of pANT5 as a 2 kb fragment after digestion with XhoI. This fragment has been designated pCIB137 and has been deposited with the USDA Agricultural Research Service Culture Collection, Northern Regional Research Center (NRRL).

The recombinant DNA sequences of the present invention may be chimeric and may be heterologous or homologous. The recombinant DNA sequences of the present invention may further comprise one or more regulatory DNA sequences operably linked to the structural DNA sequence above. Such regulatory DNA sequences include promoter sequences, leader sequences, and other DNA sequences which may affect the expression of the regulatory DNA sequences, as well as those fragments of a regulator DNA sequence that are able to act with such effect.

B: Mutant Complementation with the lemA Gene

Of the eight pleiotropic mutants isolated, five are not complemented by plasmids carrying the gafA gene indicating that at least one other genetic locus is required for gene activation. A total gene library of strain 915 was introduced into these mutants (e.g. CGP 21) by conjugation and transconjugants which had regained wildtype morphology are obtained. These transconjugants also produced pyrrolnitrin, chitinase, and cyanide. The restoring clones are isolated from the transconjugants and characterized. A 6 kb subclone which encodes a gene with high homology to lemA (Hrabak et al., (1992) supra) was found to retain the phenotype restoration ability. This clone was deposited as pCIB168. Consequently the lemA gene clearly has the ability to restore the biocontrol phenotype in these pleiotropic mutants. However, when the lemA gene was introduced into strain 914 it was not capable of activating latent gene expression, corroborating the assertion that strain 914 does not produce chitinase, gelatinase, pyrrolnitrin and cyanide because of inadequate gafA expression. By way of corollary, lemA would predictably activate latent gene expression in strains of Pseudomonas in which lemA expression is the rate-limiting factor preventing the production of chitinase, gelatinase, pyrrolnitrin and cyanide. Other bacterial genes functionally homologous to lemA would be able to act in the same way as lemA. Such genes comprise a class of sensory component genes capable of phosphorylating and therefore activating the gafA class of activators described above. Members of the class can be identified and isolated by complementation of the appropriate class of pleiotropic mutants as described herein. For example, the corresponding E. coli gene responsible for the phosphorylation of uvrY is one such gene.

Clearly the gene activating sequences gafA and lemA play pivotal roles in the activation of a series of genes involved in the production of enzymes and metabolites important in the biocontrol phenotype of Pseudomonas.

The rpoS gene: An Additional Gene Activating Sequence

In Escherichia coli, it has been demonstrated that an alternate sigma factor designated rpoS is required for the transcription of a large set of genes which are preferentially expressed during stationary phase conditions (i.e. conditions of nutrient stress) (Siegele and Kolter, I. Bacteriol. 174:345–348 (1992); Hengge-Aronis, Cell 72:165–168 (1993)). The homologue of the E. coli rpoS gene was isolated from the P. fluorescens strain 915. The DNA sequence of the P. fluorescens strain 915 rpoS gene and the deduced amino acid sequence of the rpoS sigma factor are provided as Sequence ID No. 8 and Sequence ID No. 9, respectively. The deduced amino acid sequence is greater than 86% identical to that of the unpublished sequence of a Pseudomonas aeruginosa rpoS gene (Tanaka and Takahashi, Genbank accession #D26134, (1994)). It is also highly homologous to the E. coli, Salmonella typhimurium, and Shigella flexneri RpoS sigma factors (Mulvey and Loewen, Nucleic Acids Res. 17:9979–9991 (1989), GenBank accession #U05011, GenBank accession #U00119).

According to the present invention the rpoS gene may be used to stimulate biocontrol factors and secondary metabolites. The expression pattern of rpoS can be altered by placing it behind bacterial regulatory elements. Altering the temporal expression of rpoS, which is itself normally induced at the onset of stationary phase (Tanaka et al., Proc. Natl. Acad. Sci. 90:3511–3515 (1993)) has the effect of inducing expression of rpoS regulated genes earlier than normal, leading to increased production of biocontrol factors and other secondary metabolites with biological activity. This results, for example in enhanced production of pyrrolnitrin, chitinase, cyanide, gelatinase, etc. and increases the biocontrol efficacy of *P. fluorescens* strain 915 and heterologous strains with rpoS-regulated biocontrol factors. The rpoS gene with altered expression may be cloned into broad-host-range plasmids, shuttle vectors, etc. for introduction by conjugation, transformation, electroporation, transduction, etc. into a wide variety of bacteria for the stimulation of secondary metabolites, exported enzymes, etc. as a screening strategy for new biocontrol agents and novel metabolites with biological activity (antifungal, insecticidal, herbicidal, anti-bacterial, etc).

It is a further aspect of the present invention that improved biological control strains can be identified following the introduction of transcriptional activators of the rpoS class into a variety of environmental isolates. This approach represents a method for the identification of potentially effective biocontrol strains which would otherwise not be selected by any of the screening methods currently available.

Those skilled in the art will also be aware that it will be possible to improve a biological control strain by placing additional genes under the control of transcriptional activators of the rpoS class. This can be accomplished by identifying the rpoS-responsive promoter element(s) and operably linking the desired gene or genes to such element(s) before introducing such genes into the desired strain.

The Use of Gene Activating Sequences for Plant Pathogen Control

In another embodiment of the present invention, biocontrol agents are provided which are able to inhibit the growth of fungal pathogens, such as *Rhizoctonia solani*, *Helminthosporium gramineae* and species of the genera *Pythium* and *Fusarium*. These biocontrol agents may be bacteria, plant cells or animal cells transformed with the recombinant DNA sequences above, but are preferably bacterial strains, and more preferably gram negative bacterial strains, such as the pseudomonads. Most preferred as the biocontrol agent are strains of the species *Pseudomonas fluorescens*.

Another embodiment of the present invention provides methods of inhibiting the growth of fungal pathogens, such as *Rhizoctonia solani*, *Helminthosporium gramineae* and species of the genera *Pythium* and *Fusarium*. In the methods of the present invention, the gene activating DNA sequences can be introduced into the genome of a bacterial strain which may not ordinarily be effective as an inhibitor of fungal pathogens, resulting in an effective biocontrol strain.

DNA in the form of plasmids can be transferred from one bacterium to another by a sexual process termed conjugation. Plasmids capable of conjugal transfer contain genes that code for the synthesis of sex pili. Sex pili are hollow tubes that join the plasmid-containing bacterium (the donor) with another bacterium (the recipient) and through which replicated copies of the plasmid pass from the donor to the recipient. This procedure occurs naturally in nature and is utilized in the laboratory as a method of transferring genes from one bacterium to another. For some strains of bacteria, such as Pseudomonas, conjugal transfer of DNA is the preferred method since these bacteria are not readily transformed with extraneous DNA.

In yet another embodiment of the present invention, methods are provided for producing antibiotic substances which are effective in inhibiting the growth of fungal pathogens, such as *Rhizoctonia solani*, *Helminthosporium gramineae* and species of the genera *Pythium* and *Fusarium*. This method comprises introducing the recombinant DNA sequences of the present invention into the genome of a biocontrol agent to form a transformed biocontrol agent, allowing the transformed biocontrol agent to produce antibiotic substances, such as pyrrolnitrin, and extracting the antibiotic substance from the transformed biocontrol agent.

The present invention embraces the preparation of antifungal compositions in which one or more of the transformed biocontrol bacterial strains are used as active ingredient. The present invention further embraces the preparation of antifungal compositions in which the active ingredient is the antifungal metabolite or antibiotic compound produced by the transformed biocontrol agent of the present invention. Where the active ingredient is a biocontrol bacterial strain, the biocontrol preparation may be applied in any manner known for seed and soil treatment with bacterial strains. The bacterial strain may be homogeneously mixed with one or more compounds or groups of compounds described herein, provided such compound is compatible with bacterial strains. The present invention also relates to methods of treating plants, which comprise application of the bacterial strain, or antifungal compositions containing the bacterial strain, to plants.

The active ingredient of the present invention may also be an antifungal metabolite, such as an antibiotic compound, produced by the biocontrol gents of the present invention. The present invention also relates to methods of treating plants, which comprise application of the antifungal metabolite, such as an antibiotic compound, or antifungal compositions containing the metabolite, to plants.

The active ingredients of the present invention are normally applied in the form of compositions and can be applied to the crop area or plant to be treated, simultaneously or in succession, with further compounds. These compounds can be both fertilizers or micronutrient donors or other preparations that influence plant growth. They can also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying active ingredients of the present invention or an agrochemical composition which contains at least one of the active ingredients is leaf application. The number of applications and the rate of application depend on the intensity of infestation by the corresponding pathogen (type of fungus). However, the active ingredients can also penetrate the plant through the roots via the soil (systemic action) by impregnating the locus of the plant with a liquid composition, or by applying the compounds in solid form to the soil, e.g. in granular form (soil application). The active ingredients may also be applied to seeds (coating) by impregnating the seeds either with a liquid formulation containing active ingredients, or coating them with a solid formulation. In special cases, further types of application are also possible, for example, selective treatment of the plant stems or buds.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouting are chosen in accordance with the intended objectives and the prevailing circumstances. Advantageous rates of application are normally from 50 g to 5 kg of active ingredient (a.i.) per hectare ("ha", approximately 2.471 acres), preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants re nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

The agrochemical compositions usually contain from about 0.1 to about 99%, preferably about 0.1 to about 95%, and most preferably from about 3 to about 90% of the active ingredient, from about 1 to about 99.9%, preferably from abut 1 to about 99%, and most preferably from about 5 to about 95% of a solid or liquid adjuvant, and from about 0 to about 25%, about 0.1 to about 25%, and most preferably from about 0.1 to about 20% of a surfactant.

Whereas commercial products are preferably formulated as concentrates, the end user will normally employ dilute formulations.

FURTHER USES OF GENE ACTIVATING SEQUENCES

This invention also describes a novel technique for the isolation of APS biosynthetic genes which utilizes the Gene Activating Sequences which control their expression. In this method, a library of transposon insertion mutants is created in a strain of microorganism which lacks the Gene Activating Sequence or has had the Gene Activating Sequence disabled by conventional gene disruption techniques. The insertion transposon used carries a promoter-less reporter gene (e.g. lacZ). Once the insertion library has been made, a functional copy of the Gene Activating Sequence is transferred to the library of cells (e.g. by conjugation or electroporation) and the plated cells are selected for expression of the reporter gene. Cells are assayed before and after transfer of the Gene Activating Sequence. Colonies which express the reporter gene only in the presence of the Gene Activating Sequence are insertions adjacent to the promoter of genes regulated by the Gene Activating Sequence. Assuming the Gene Activating Sequence is specific in its regulation for APS-biosynthetic genes, then the genes tagged by this procedure will be APS-biosynthetic genes. In a preferred embodiment, the cloned Gene Activating Sequence is the gafA gene described in PCT application WO 94/01561 which regulates the expression of the biosynthetic genes for pyrrolnitrin. Thus, this method is a preferred method for the cloning of the biosynthetic genes for pyrrolnitrin.

It is recognized that the gene activating sequences of the present invention can be used in a variety of microorganisms to induce the production of gene products and secondary metabolites. The activating sequences are capable of inducing or enhancing the expression of genes which may be latent or natively expressed at low levels. The activating sequences may be used individually or in various combinations to induce or enhance expression of the genes they regulate. Preferred for use as gene activating sequences in such methods are the gafA, lemA and rpoS genes and combinations thereof.

As discussed above, the activating elements find use in the production of antibiotics in microorganisms for the purposes of biocontrol. Such elements are also useful in the production of antibiotics for pharmaceutical purposes, particularly in strains of microorganisms which natively express the biosynthetic genes at low levels or not at all. Examples of strains suitable for manipulation in this manner include strains of Streptomyces for the production of tetracycline, erythromycin, chloromycetin, and streptomycin; strains of Bacillus for the production of bacitracin; and strains of Penicillium for the production of penicillin.

The activating elements find further use in the production of vitamins, growth factors and hormones in selected strains of microorganisms. Examples include the enhanced production of vitamin B2 and B12 from Ashbya and Streptomyces, respectively; the production of gibberellin from Fusarium and Gibberella; the production of 11-α-hydroxyprogesterone from Rhizopus; and the production of corticosterone from Curvularia.

Other applications include but are not limited to the enhanced production of butanol, acetone, and ethanol from Clostridium; the production of glycerol from Saccharomyces; the production of lactic acid from Lactobacillus; the production of polysaccharides such as alginate, xanthan, dextran from Leuconostoc and other organisms; the production of secreted proteins and enzymes such as amalyses, proteases, pectinases, chitinases, cellulases, gelatinases, collagenases, elastases, etc. from Bacillus, Aspergillus and other organisms; and the production of invertase from Saccharomyces.

The following examples are offered by way of illustration and not by way of limitation.

EXAMPLES

Example 1

Mutant Isolation and Functional Complementation

The wild-type *Pseudomonas fluorescens* strain 11c-1-38 (strain 915) was mutated by exposure to the mutagen N-Methyl-N'-nitro-N- nitrosoguanidine. Approximately two dozen antibiotic-affected mutants were identified by screening individual mutants for their ability to inhibit the growth of *P. ultimum* and *R. solani* on nutrient agar. Most of these were shown to have reduced, or no, antibiotic activity against one of the two phytopathogenic fungi, but were not affected in their inhibition of the other fungus. However, one mutant, that we have named mutant 2-1, was found to lack antibiotic activity against both test fungi. These results strongly indicated that *P. fluorescens* strain 11c-1-38 produced two distinct antibiotics, one effective against *P. ultimum* and the other effective against *R. solani*, rather than one antibiotic that was effective against both fungi.

A gene library of total DNA isolated from the parent strain was constructed by partial SalI restriction of the DNA, size fractionation to yield fragments of 20–30 kilobases, and ligation into XhoI-restricted vector pVK100. Knauf et al., *Plasmid* 8:45–54 (1982). The gene library was transferred to the antibiotic mutant 2-1 by triparental conjugation with *E. coli* harboring the tra$^+$ plasmid pRK2013. Ditta et al., *Proc. Natl. Acad. Sci. USA* 77:7347–7351 (1980). Transgenic exconjugants were tested for the production of antibiotic by measuring growth inhibition of *P. ultimum* and *R. solani*. Three overlapping clones were identified that restored antibiotic activity against *R. solani*, but not against *P. ultimum*, to mutant 2-1. Restriction maps of these clones were determined and are shown in FIG. 1.

Example 2

Characterization of the E11 gene region.

Figure 2:
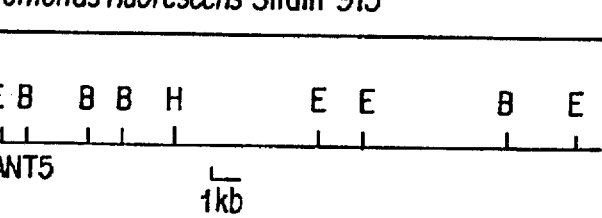
FIG. 2: This figure shows the ability of DNA subfragments derived from the pANT5 clone of *Pseudomonas fluorescens* strain 915 to complement the ANT⁻ phenotype of mutant 2-1 and the wild type strains 914 and 922. The subfragment labeled 3 is the approximately 11 kb region which has been called the E11 fragment.

The genetic region necessary for the functional complementation of antibiotic biosynthesis in mutant 2-1 was defined by subcloning portions of the larger region and assessing their ability to complement mutant 2-1 for antibiosis (FIG. 2). The smallest fragment that was demonstrated to complement the mutation was the 4.9 kb HindIII/EcoRI fragment, which was indicated as subfragment 6 in FIG. 2 and was designated subfragment H/E4.9. Some of the subcloned DNA fragments derived from the antibiotic gene parent clone, which was designated pANT-5, were transferred to two wild type *P. fluorescens* strains, 11c-1-33 (strain 914) and 11-1-6 (strain 922), that were not ordinarily able to produce antibiotic against *R. solani*.

The results, shown in FIG. 2, indicated that an 11 kb EcoRI subfragment, which is indicated as subfragment 3 in FIG. 2 and was designated subfragment E11, imparts *R. solani*-active antibiosis to both strains.

Example 3

Inhibition of *Rhizoctonia solani*

An active antibiotic compound can be extracted from the growth medium of the transformed *P. fluorescens* strain that produces this antibiotic. This was accomplished by extraction of the medium with 80% acetone followed by removal of the acetone by evaporation and a second extraction with diethyl ether. The diethyl ether was removed by evaporation and the dried extract is resuspended in a small volume of water. Small aliquots of the antibiotic extract applied to small sterile filter paper discs placed on an agar plate will inhibit the growth of *R. solani*, indicating the presence of the active antibiotic compound. The antibiotic was determined by NMR and mass spectrometry to be pyrrolnitrin.

Example 4

Description of the pleiotropic defects restored by fragment E11 and by the 2. 0 kb XhoI subfragment; ability of these fragments to activate latent genes in other bacterial strains.

The mutant derivative of *P. fluorescens* strain 915 designated mutant 2-1 was initially isolated on the basis of its reduced ability to inhibit the growth of the fungus *Rhizoctonia solani* in vitro. The production of an antibiotic metabolite, subsequently identified as pyrrolnitrin, was lacking in mutant 2-1. While lack of pyrrolnitrin production was the first defect observed in mutant 2-1, additional experimentation, details of which are described below, reveal that mutant 2-1 is a member of one class of pleiotropic mutants with characteristics summarized in Table 1.

a) Loss of pyrrolnitrin production

*P. fluorescens* strain 915 and mutant 2-1 were tested for pyrrolnitrin production by growing the respective cultures for three days in 50 ml of nutrient broth containing AMBERLITE XAD-4 resin (Robin and Haas) (5% v/v) at 28 C. The resin was collected in a sieve and washed extensively with water. The pyrrolnitrin was eluted from the resin by two consecutive extractions with isopropanol (0.5X volume). The two extractions were combined and desiccated under vacuum in a rotary evaporator at 40 C. The desiccated material is dissolved in 2 ml of isopropanol and was further analyzed by HPLC chromatography using a Hypersil ODS column (2.1 mm dia.×10 cm) with a mobile phase consisting of a water/methanol mixture with a starting composition of 0/100% and gradually changing to a final composition of 100/0%. Prior to injection into the HPLC, 100 ul of each extract was desiccated under vacuum and resuspended in the same volume of water/methanol (50/50). The material eluting from the column was monitored by B absorbance at 212 nm and at 252 nm, and was fractionated by elution time. *P. fluorescens* strain 915 extracts contained a peak which comigrates with a pyrrolnitrin standard and which was determined to be pyrrolnitrin by NMR spectroscopy and by mass spectrometry. Mutant 2-1 and the other identified pleiotropic mutants lack this peak.

b.) Loss of cyanide production

*P. fluorescens* strain 915 and mutant 2-1 and additional pleiotropic mutants were tested for the production of cyanide. Pieces of Whatman paper were impregnated with 5 mg/ml chloroform cupric ethyl acetoacetate and 5 mg/ml chloroform 4,4'-methylene bis-(N,N dimethyl aniline) and chloroform was allowed to evaporate. Papers were then placed under the covers of microtiter plates whose wells have been inoculated with cultures of strain 915 and the various pleiotropic mutants. Plates are wrapped in aluminum foil and incubated overnight at 28 C. The paper turned a blue color above the well of each culture producing cyanide. The results indicated that strain 915 produced cyanide, while the pleiotropic mutants failed to produce cyanide.

c.) Loss of chitinase production

*P. fluorescens* strain 915 and various pleiotropic mutants were tested for the presence of chitinase activity by either of two methods. In the first method, 300 ml L-broth cultures of each strain were incubated at 28 C. for 12 hours. Cells were collected by centrifugation and washed once in 20 mM phosphate buffer (10 mM Na2HPO4/10 mM KH2PO4). Following centrifugation, the cell pellets were resuspended in 5 ml of the 20 mM phosphate buffer. Cells were lysed by sonication for 60 seconds with the microtip of a Branson sonifier and cell debris is removed from the cell extracts by centrifugation. Chitinase activity was assayed by incubation of 100 ul of cell extract with 100 ul of tritiated chitin (0.5% w/v; approximately 0.1 mCi/ml) in a 250 ul total volume of 0.03M sodium phosphate, pH 6.5 for 1 hour at 37 C. The reaction was stopped by addition of an equal volume of 2M TCA, followed by centrifugation. 200 ul aliquots were counted in a liquid scintillation counter to determine soluble counts released from the insoluble chitin molecules as a result of chitinase activity. Typical results, presented in Table 2, indicate that a transposon mutant designated #736, which proved to be a member of one class of pleiotropic mutants, lacks the chitinase activity found in *P. fluorescens* strain 915.

TABLE 2

| STRAIN | COUNTS/MINUTE |
|---|---|
| *P. fluorescens* 915 | 32205 |
| Transposon mutant # 736 | 4366 |
| No extract | 4993 |

In the second method, 200 ul cultures of each strain were grown overnight at 28 C. in L-broth in the wells of a 96-well microtiter plate. The overnight cultures were frozen and allowed to thaw before further use to release some enzyme which might otherwise be cell-bound. 10 ul of 0.5 mM 4-methylumbelliferyl beta-D-N,N'-diacetylchitobioside was added to the wells of an opaque black microtiter plate containing 10 ul of each overnight bacterial culture and 80 ul of a solution consisting of 50 mM sodium phosphate, pH 7.0; 10 mM EDTA, 0.1% Triton X-100, 0.1% Sarkosyl, and 10 mM beta-mercaptoethanol. Incubation was for 3 hours at 37 C. Release of fluorescent methylumbelliferyl groups by chitinase activity was monitored by reading the microtiter plates at an excitation of 355 nm and an emission of 460 nm on a Titertek Fluoroscan II fluorescent spectrophotometer. Typical results, presented in Table 3, indicate that pleiotropic mutants lack the chitinase activity found in *P. fluorescens* strain 915.

TABLE 3

| STRAIN | FLUORESCENCE UNITS |
|---|---|
| *P. fluorescens* 915 | 13.2 |
| Pleiotropic mutant | 0.687 | d.) Reduction in gelatinase activity

Gelatinase activity of *P. fluorescens* strain 915 and various pleiotropic mutant derivatives was assayed by incubating the bacteria on nutrient agar plates supplemented with 3% w/v Bacto-gelatin (Difco). A cloudy halo forms in the agar surrounding colonies synthesizing and exporting a protease capable of hydrolyzing the gelatin. Prominent halos appeared around colonies of strain 915 following 24 hour incubation at 28 C. Such halos failed to appear around colonies of the pleiotropic mutants within the 24 hour time period, appearing instead after approximately 48 hours. Thus, while the pleiotropic mutants are not totally devoid of gelatinase activity, they either fail to synthesize the species of protease which appears in strain 915 within 24 hours, or else the synthesis and/or export of that species is delayed.

e.) Alteration in colony morphology

On minimal growth medium, *P. fluorescens* strain 915 forms small, circular, convex white opaque colonies with entire edges. All pleiotropic mutants examined thus far formed larger, circular, flat, translucent colonies with undulate edges.

Example 5

Analysis of the 11 kilobase fragment (E11)

FIG. 3 depicts the genetic organization of the 11 kilobase fragment E11 determined to date from DNA sequence analysis. A variety of subclones of fragment E11 were prepared as double-stranded templates for dideoxy sequencing reactions by digestion of fragment E11 with various restriction endonucleases, either singly or in combination, followed by ligation with appropriate cloning vectors such as pBS SK+ (Stratagene). As regions of contiguous DNA sequence were generated, they are compared against sequences contained in the GenBank database for homology with known bacterial gene coding regions. This analysis has thus far led to the assignment of the genetic organization for fragment E11 depicted in FIG. 3. ORF 1 shares substantial homology with the cheR gene of E. coli and the frzF gene of Myxococcus xanthus. cheR in E. coli has a methyl transferase activity which is involved in mediating the chemotaxis response (Springer and Koshland, Proc. Natl. Acad. Sci. USA 74:533–537) and frzF appears to have a similar function in M. xanthus (McCleary et al., J. Bacteriol. 172:4877–4887 (1990)). ORF 2 shares substantial homology with numerous genes encoding sensor components of so-called bacterial two-component regulatory sequences (Albright et al., 1989; Bourret et al., 1991; and Mekalanos, 1992). Examples of other bacterial sensor component genes include cheA of E. coli, rcsC of E. coli, frzE of Myxococcus xanthus, and bvgS of Bordetella pertussis. The P. fluorescens strain 915 glyW tRNA gene is 100% homologous to the glyW tRNA locus of E. coli. ORF 3 shares substantial homology with the pgsA gene of E. coli which encodes phosphatidyl glycerophosphate, an enzyme involved in phospholipid metabolism (Gopalakrishnan et al. , J. Biol. Chem. 261:1329–1338 (1986)). ORF 4 shares substantial homology with the uvrC gene orE. coli which encodes a component of the ultraviolet light damage repair excinuclease (Sharma et al., Nucl. Acids Res. 14:2301–2318 (1986)).

ORF 5, which is present on the gene-activating 2.0 kb XhoI subclone of fragment E11, shares substantial homology with numerous genes encoding transcription activator components of bacterial two-component regulatory sequences. In particular, ORF 5 is highly similar to the gacA gene of Pseudomonas fluorescens CHA0 (Laville et al., 1992) and to the uvr-23 gene of E. coli (Moolenar et al., 1987). Examples of some other bacterial transcriptional activator genes with sequence similarity to ORF 5 include sacU of Bacillus subtilis, bvgA of Bordetella pertussis, and algR of Pseudomonas aeruginosa. The entire coding region of ORF 5 is presented as SEQUENCE ID NO. 1. The entire sequence of a. 5.6 kilobase portion of fragment E11, bounded by the left-most EcoRI site depicted in FIG. 3 and by an internal HindIII site, is presented as SEQUE ID 2. The coordinates of open reading flames contained in sequence ID 2 are as follows:

ORF 1: 210–1688; transcribed left to right
ORF 2: 1906–3633; transcribed left to right
glyW: 4616–4691; transcribed right to left
ORF 3: 4731–5318; transcribed right to left The combined results that the 2.0 kb XhoI subclone of fragment E11 containing ORF 5 activates latent gene expression in Pseudomonas strains and that the E. coli uvr-23 gene, which is homologous to ORF 5, is capable of activating latent Pseudomonas gene expression indicate that transcriptional activators of the ORF 5 class have the unexpected capability of activating the expression of latent bacterial genes.

Example 6

Cloning of 2 kb fragment

The mutant strain 2-1 was derived from the biocontrol Pseudomonas strain 915 following N-Methyl-N'-nitro-N-nitrosoguanidine treatment. It is initially identified on the basis of its inability to inhibit the growth of the fungi Rhizoctonia solani and Pythium ultimum in vitro. Further characterization revealed that the strain was also defective in the expression of a number of activities, including pyrrolnitrin, chitinase, and cyanide production. In addition, mutant 2-1 is morphologically distinguishable from strain 915. On agar plates containing the defined medium LMG (0.1% $KH_2PO_4$, 0.1% $Na_2HPO_4$, 0.1% NaCl, 0.4% $(NH_4)_2SO_4$, 0.02% glucose and 0.66% $MgSO_4$, and 1.6% agar) the wild type parent (strain 915) formed small, circular, convex, white opaque colonies with entire edges. Mutant 2-1 formed larger, circular, flat, translucent colonies with undulate edges.

The approximately 2 kb XhoI fragment containing ORF5 was cloned into the broad host range plasmid pVK100 (Knauf et al., (1982), Plasmid 8:45–54) to yield the plasmid pCIB137.

Example 7

Analysis of the 2 kilobase XhoI fragment

Comparison of the ORF5 sequence to DNA sequences in the GenBank database revealed substantial homology with numerous transcription activator genes in known bacterial two-component regulatory systems. In particular, ORF5 is highly similar to the gacA gene of Pseudomonas fluorescens CHA0 and to the uvr-23 gene of E. coli ORF5 is located entirely within an approximately 2 kb region defined by XhoI restriction sites. This approximately 2 kb XhoI fragment was cloned into the broad host range plasmid pVK100 (Knauf et al. (1982), Plasmid 8:45–54) to yield the plasmid pCIB137. pCIB137 was deposited with the USDA Agricultural Research Service Culture Collection, Northern Regional Research Center (NRRL) at 1815 North University Street, Peoria, Ill. 61604 on Jun. 24, 1992 and has been accorded the accession number B-18981.

pCIB137 was introduced into the E. coli host strain S17-1 (Simon et al. (1983), Biotechnology 1:784–791) by transformation. It was then transferred into strain 2-1 by conjugation. Fresh overnight cultures of S17-1(pCIB137) and strain 2-1 were mixed (50 μl each) on an L agar plate and allowed to incubate overnight at 28C. Loopfuls of bacteria from the mating mixture were then streaked on LMG agar containing 15 μg/ml tetracycline and further incubated at 28 C. Tetracycline resistant colonies were purified and examined for the presence of pCIB137. Transconjugants of strain 2-1 containing pCIB137 were shown to produce pyrrolnitrin, chitinase, and cyanide. They also display the morphology of strain 915.

The natural Pseudomonas isolates strain 914 and strain 922 do not produce detectable levels of pyrrolnitrin, chitinase, or cyanide. They formed large, circular, flat, translucent colonies with undulate edges on LMG agar. pCIB137 is introduced into these strains by conjugation as described in example 2. Transconjugants of strain 914 containing pCIB137 were shown to produce pyrrolnitrin, chitinase, and cyanide. They also displayed the morphology of P. Fluorescens strain 915. Transconjugants of strain 922 containing pCIB137 were also shown to produce pyrrolnitrin, chitinase, and cyanide, but they did not display a change in morphology. Thus, it was shown that the introduction of pCIB137 into Pseudomonas fluorescens strains (e.g. strain 914 and strain 922) which are ineffective in the in vitro or in vivo inhibition of P. Rhizoctonia solani, unexpectedly activated expression of previously inactive, undetected chitinase, cyanide, and pyrrolnitrin genes, and converted these strains into effective biocontrol agents in greenhouse assays. Also, in the case of strain 914, introduction of fragment E11 unexpectedly caused a conversion in colony morphology to one very similar to that listed for *P. fluorescens* strain 915 in Table 1.

Example 8

Intact ORF 5 is necessary for gene activation

DNA sequence analysis revealed the presence of two NaeI recognition sites, located 72 bp apart, within ORF5. Removal of the intervening DNA reduces the predicted gene product by 24 amino acids and may render the gene product nonfunctional. The 2 kb XhoI fragment was cloned into the XhoI site of the plasmid pSP72 (Promega). The resulting construct, designated pCIB138, contains no other NaeI sites besides the two in ORF5. Digestion of pCIB138 DNA with NaeI followed by ligation at a concentration of 30 ng/µl and transformation into *E. coli* strain S 17-1 yielded pCIB150, which contains the desired 72 bp deletion. The presence of the deletion was confirmed by DNA sequencing. The ORF5-containing XhoI fragment from pCIB150 was cloned into PVK100 to yield pCIB149. pCIB149 is identical to pCIB137 except for the deletion of the 72 bp of DNA. When pCIB149 was introduced into strains 914 and 922 by conjugation as described in example 5, pyrrolnitrin, chitinase, or cyanide production was not detected. Thus, an intact ORF5 is necessary for gene activation in bacterial strains.

Example 9

Gene-Replacement Experiment

The effect of ORF 5 on gene regulation in strain 915 was demonstrated by the following gene-replacement experiment. The right 6.8 kb of fragment E11 (bounded by right-most EcoRI and BamHI sites, see FIG. 3) was cloned into pBR322 (digested with EcoRI and BamHI) to form pBREB6.8. The 2 kb XhoI fragment containing ORF 5 was removed from pBREB6.8 by digestion with XhoI, then self-ligation to form pCIB139. A kanamycin resistance marker was introduced into pCIB139 by substituting the HindIII-SalI kanamycin resistance fragment from Tn5 for the tetracycline resistance region bounded by HindIII and SalI in pCIB139. The resulting plasmid, pCIB154, was used to receive the 2 kb XhoI fragment (with the 72 bp NaeI deletion) from pCIB150 to form pCIB156. This plasmid was transformed into the *Escherichia coli* strain S17-1 (Simon et al. (1983) BioTechnology 1:784–791), then introduced into strain 915 by conjugation, selecting for kanamycin resistance. Since pCIB156 cannot be maintained autonomously in strain 915, the kanamycin resistant transconjugants contained the plasmid, and its kanamycin resistant determinant, integrated into the chromosome. The most frequent integration events took place by homologous recombination and at the region of homology provided by the 2 kb XhoI fragment and its surrounding sequences. Such transconjugants contain two copies of the 2 kb XhoI region, one wildtype and one with the 72 bp NaeI deletion. Such duplications are unstable in bacteria with a proficient homologous recombination system and are lost at detectable frequencies spontaneously when selective conditions favoring their formation are removed. One such transonjugant is cultured in liquid medium without kanamycin selection and then plated on solid agar medium to obtain individual colonies, again without kanamycin selection. Individual colonies were tested for kanamycin sensitivity. Such colonies were obtained at approximately 2% of the total. These kanamycin sensitive colonies fall into two morphological classes, one resembling the wildtype, the other resembling the pleiotropic mutants. Southern hybridization results confirmed that both classes of colonies had lost the integrated plasmid and that the class with the wildtype morphology contained an intact 2 kb XhoI region, while the other class contains a smaller XhoI region corresponding to that with the 72 bp NaeI deletion. Colonies of the former class were identical to strain 915. Colonies of the latter class were identical to strain 915 except for a 72 bp NaeI deletion in ORF 5. These derivatives of strain 915 no longer produce pyrrolnitrin, chitinase, or cyanide. Thus, an intact ORF 5 is necessary for gene activation in strain 915.

Example 10

The native promoter of ORF 5 is contained within the 2 kb XhoI fragment

The following evidence indicates a promoter element directing transcription of ORF 5 is likely to be found within the 2 kilobase XhoI fragment. A version of the broad host range plasmid pVK100 containing the 2 kb XhoI fragment was isolated with the 2 kb insert in the opposite orientation from that found in pCIB137. This plasmid was designated pCIB151. Introduction of pCIB151 into pleiotropic mutants and into *P. fluorescens* strain 914 activated gene expression. The ability of the 2 kb XhoI fragment to activate gene expression in each orientation, and the previously described requirement of functional ORF 5 gene product for gene activation, made it likely that transcription of ORF 5 relies on the presence of a promoter located within the 2 kb insert. Furthermore, Moolenar et al., (1987) have identified a promoter directing transcription of the ORF 5-related uvr-23 gene or *E. coli*. This promoter was contained within the first 100 base pairs upstream of the uvr-23 structural gene. At a nearly identical position upstream of ORF 5, we have identified the sequence TTGTCA-17bp-TTTTTT which is similar to the sigma-70 promoter consensus sequence described by Rosenberg and Court, Annu. Rev. Genet. 13:319–353 (1979). The sequence of a 983 base pair region containing the ORF 5 structural gene, the possible promoter region, and the 5' end of ORF 4 (which is homologous to uvrC of *E. coli*) is presented in SEQUENCE ID 3. The coordinates of these elements in sequence ID 3 are as follows:

Sequence with promoter homology: 23-51

ORF 5 structural gene: 99-740

5' end of ORF 4 (uvrC) 743-983

It is likely that a promoter native to the 2 kb XhoI fragment was directing transcription of ORF 5 when ORF 5 was introduced into pleiotropic mutant derivatives of *P. fluorescens* 915 or into *P. fluorescens* strains 914 and 922. However, to express the ORF 5 class of transcriptional activators in some bacterial strains, one skilled in the art will recognize that it might be beneficial to operably link the structural ORF 5 class gene with a promoter and/or ribosome binding site which functions more efficiently in the desired host bacterial genus to activate latent genes. For example, to activate latent genes in Bacillus species with ORF 5 class genes, the ORF 5 class gene may be operably linked to a Bacillus regulatory region. Such regulatory regions are readily available to those skilled in the art. One possible method for accomplishing this fusion between bacterial regulatory sequences and ORF 5-class structural genes involves use of the overlap extension polymerase chain reaction strategy (Horton et al., Gene 77:61).

Example 11

Analysis of the ORF 5 Gene a) The ORF 5 coding region is capable of encoding a 213 amino acid protein with features of a bacterial transcription activator. For example, there is strong homology between domains 1. and 2 of transcriptional regulators reviewed by Albright et al. (1989) and comparable regions in ORF 5. The predicted aspartic acid residue at position 54 of the protein lines up with the conserved aspartic acid residues of other transcriptional activators of this class. It is the aspartic acid at this position which is typically phosphorylated by interaction with a sensor component protein. Alignment of ORF 5 with uvr-23 of E. coli and with gacA of P. fluorescens CHA0 leads to the conclusion that ORF 5 contains the unusual translation start codon TTG, which is less efficient than either ATG or GTG start codons. It is worth noting that at amino acid position 49 of ORF 5 resides an aspartic acid residue, while a tyrosine residue is present at the equivalent position of gacA. In virG, an *Agrobacterium tumefaciens* transcriptional activator, an asparagine to aspartic acid substitution near the conserved phosphorylation site converted virG to a constitutive transcription activator which presumably no longer required phosphorylation by a sensor component. It is possible that our ORF 5 is such a constitutive activator by virtue of the substitution of aspartic acid for tyrosine.

b) As noted above, a promoter directing transcription of ORF 5 likely resides within the 2 kb XhoI fragment. It is possible to map the location of this promoter by, for example, a combination of S 1 nuclease mapping (Aiba et al., J. Biol. Chem. 256:11905–11910 (1981)) and primer extension mapping (Debarbouille and Raibaud, J. Bacteriol. 153:1221–1227 (1983)) as was done for a different Pseudomonas promoter by, for example, Gaffney et al., J. Bacteriol. 172:5593–5601 (1990). Once located, a DNA fragment containing this promoter can be operably linked if desired to ORF 5-class activators either by ligation of the appropriate DNA restriction fragments or by the overlap extension primer extension method of Horton et al.

c) Bacterial regulatory elements can be obtained from various sources including commercially available vectors, bacterial regulatory elements known in the art, and bacterial regulatory elements identified using promoterless marker-containing transposons, or promoter selection vectors such as pKK175-6 and pKK232-8 (Pharmacia, Piscatoway, N.J.). Commercially available bacterial regulatory elements are available from a number of sources such as the plasmid expression vectors pKK233-2, pDR540, pDR720, pYEJ001, pPL-lambda (Pharmacia), or pGEMEX expression vectors (Promega Biotec, Madison, Wis.). Bacterial regulatory elements known in the art include any bacterial regulatory element that is known to function as a promoter, enhancer, ribosome binding site, and/or any other regulatory control mechanism of the associated coding DNA sequence. An associated coding DNA sequence is a DNA sequence that is adjacent or adjoining 3' to the regulatory elements and which codes for a protein when transcribed and translated. Appropriate bacterial elements include those of Deretic et al., Bio/Technology 7:1249–1254 (1989); Deuschle et al., EMBO J. 5:2987–2994 (1986); Hawley and McClure, Nucleic Acids Res. 11:2237–2255 (1983); Rosenberg and Court, Annu. Rev. Genet. 13:319–353 (1979), and references cited therein. Likewise, promoters for use in gram positive microorganisms such as Bacillus species are readily accessible to those skilled in the art. Any of the above can be synthesized using standard DNA synthesis techniques. Bacterial regulatory elements include hybrid regulatory regions comprising mixtures of parts of regulatory elements from different sources. For example, the trp/lac (trc) promoter of pKK232-2 (Pharmacia) which combines the -35 region of the E. coli tryptophan operon promoter with the -10 region of the E. coli lac operon promoter functions effectively in Pseudomonas (Bagdasarian et al., Gene 26:273–282 (1983).

Certain bacterial promoters have the capability of functioning efficiently in a variety of bacterial genera. For example, promoters for selectable markers on the broad-host-range plasmid RSF1010 are known to function in at least the following bacterial genera: Acetobacter, Actinobacillus, Aerobacter, Aeromonas, Agrobacterium, Alcaligenes, Azotobacter, Azospirillum, Caulobacter, Desulfovibrio, Erwinia, Escherichia, Gluconobacter, Hyphomicrobium, Klebsiella, Methylophilus, Moraxella, Paracoccus, Proteus, Pseudomonas, Rhizobium, Rhodobacter, Serratia, Xanthomonas, Vibrio, Yersinia, and Zymomonas (Morales et al., 1990. In: Pseudomonas: Biotransformations, Pathogenesis, and Evolving Biotechnology, (Silver, Chakrabarty, Iglewski, and Kaplan, eds.) pp. 229–241.)

Example 12

Biocontrol Efficacy of Transgenic Strains

Biocontrol efficacies of the pCIB137-containing transconjugants of strains 914 and 922 were compared to their natural parents. Bacterial cultures were grown overnight in Luria broth at 28 C. Cells were pelleted by centrifugation, then resuspended in sterile water to an optical density of 2.5 at 600 nm (approximately $2 \times 10^9$ colony forming units per ml.). *Rhizoctonia solani* was cultured on autoclaved millet, then dried and ground into powder. Soil was prepared by mixing equal parts of potting soil (Metro-mix 360), sand, and vermiculite. This was used to fill 15 cm diameter pots. A 2 cm deep circular furrow with a total length of 30 cm was formed at the perimeter of each pot. Ten cotton seeds (stoneville 506) were placed in each furrow. *R. solani*-infested millet powder was sprinkled evenly over the seeds in the furrows at the rate of 100 mg/pot, followed by the application of 20ml of bacterial suspension for each pot. Water was added in place of bacterial suspension in the unbacterized control. Each treatment consisted of four replicate pots for a total of 40 seeds per treatment. The plants were grown in an environmentally controlled chamber with a day/night temperature regime of 26/21 C. The plants were rated for disease severity after 10 days. The results (Table 4) clearly indicate that strains 914 and 922 provide no disease control, whereas their pCIB137-containing transconjugants provided good control of *R. solani* in cotton.

TABLE 4

| | (Stand 10 DAPa) | | | | | |
|---|---|---|---|---|---|---|
| Treatment | Rep1 | Rep2 | Rep3 | Rep4 | Mean | % Biocontrol |
| NP.NTb | 9 | 10 | 9 | 9 | 9.25 | 100.0 |
| P.NTc | 0 | 2 | 1 | 1 | 1.00 | 0.0 |
| 914 | 3 | 0 | 3 | 1 | 1.75 | 9.1 |
| 914(pCIB149) | 0 | 1 | 0 | 2 | 0.75 | -3.0 |
| 914(pCIB137) | 5 | 4 | 5 | 7 | 5.25 | 51.5 |
| 922 | 1 | 1 | 1 | 3 | 1.50 | 6.1 |
| 922(pCIB137) | 8 | 10 | 7 | 6 | 7.75 | 81.8 |

1 = Uninfested control designated 100% biocontrol; Infested control designated 0% biocontrol
a = Days After Planting
b = No Pathogen, No Treatment (Uninfested control)
c = Pathogen, No Treatment (Infested control)

Example 13

Multiple Copies of a gafA Gene Isolated from the *Pseudomonas fluorescens* Strain 914 Activate Expression of Latent Genes in Strain 914

The 2.0 kb XhoI fragment containing the gafA gene of *P. fluorescens* strain 915 was labeled and hybridized with XhoI-digested total genomic DNA from *P. fluorescens* strain 914. A 2.0 kb XhoI fragment from strain 914 which hybridized to the probe is cloned in pBluescript SK+ and DNA sequencing is performed to verify that the clone contains a gafA homologue. The DNA sequence of the gafA homologue in strain 914 is presented in Table 5. The strain 914 gafA homologue differs from the strain 915 gafA at nine nucleotide positions, but only one of these nucleotide differences is predicted to generate an amino acid change difference in the two proteins (amino acid residue 182 is threonine in the strain 915 GalA protein and isoleucine in the 914 GafA protein). The strain 914 gafA gene was subcloned into the broad-host-range plasmid pVK100 and the resulting recombinant plasmid was introduced by conjugation into strain 914. Whereas expression of the single chromosomal gafA gene in strain 914 was not capable of activating expression of genes required for the synthesis of pyrrolnitrin, chitinase, and cyanide, strain 914 derivatives containing multiple plasmid copies of the 914 gafA gene did synthesize pyrrolnitrin, chitinase, and cyanide.

When a pLAFR3 derivative containing the *E. coli* uvr-23 gene was mobilized by conjugation into *Pseudomonas fluorescens* strain 914, the uvr-23 gene activated expression of genes involved in the production of cyanide, chitinase, and pyrrolnitrin. Optimal activation in *P. fluorescens* strain 914 apparently depends upon expression of uvr-23 from the lac promoter of pLAFR3.

Example 15

Further Delimitation of the 2.0 kb XhoI Fragment to Identify the Smallest Subunit that is Functional The fact that an *E. coli* ORF 5-like transcription activator could activate latent genes in *P. fluorescens* strain 914 (Example 12), coupled with the fact that disruption of ORF 5 in the 2.0 kb XhoI fragment abolishes the gene-activating ability of this fragment, indicates that it should be possible to define a smaller DNA fragment than the 2 kb fragment with gene-activating ability, provided ORF 5 is intact and expressed. Expression of ORF 5 can be directed either from

TABLE 5

| gafA open reading frame from pCIB 3341 |
|---|
| 1 TTGATTAGGG TGCTAGTGGT CGATGACCAT GATCTCGTTC GTACAGGTAT |
| 51 TACCCGAATG CTGGCTGACA TCGATGGCCT GCAAGTGGTC GGTCAGGCCG |
| 101 AGTCAGGGGAGGAGTCCCTGCTCAAGGCCCGGGAGTTGAAACCCGATGTG |
| 151 GTCCTCATGG ACGTCAAGAT GCCCGGGATC GGCGGTCTTG AAGCCACGCG 201 |
| CAAATTGTTG CGCAGTCACC CGGATATCAA AGTCGTGGCC GTCACCGTGT 251 |
| GTGAAGAAGA CCCGTTCCCG ACCCGCTTGC TGCAAGCCGG TGCGGCGGGT 301 |
| TACCTGACCA AAGGTGCGGG CCTCAATGAA ATGGTGCAGG CCATTCGCCT 351 |
| GGTGTTTGCC GGCCAGCGTT ACATCAGCCC GCAAATTGCC CAGCAGTTGG 401 |
| TGTTCAAGTC ATTCCAGCCT TCCAGTGATT CACCGTTCGA TGCTTTGTCC 451 |
| GAGCGWAAA TCCAGATCGC GCTGATGATT GTCGGCTGCC AGAAAGTGCA 501 |
| GATCATCTCC GACAAGCTGT GCCTGTCTCC GAAAACCGTT AATATCTACC 551 |
| GTTACCGCAT CTTCGAAAAG CTCTCGATCA GCAGCGATGT TGKACTOACA 601 |
| TTGCTGGCGG TTCGCCACGG CATGGTCGAT GCCAGTGCCT GA (SEQ ID NO: 5) |

Example 14

Activation of Latent Gene Expression with the *E. coli* uvr-23 Gene

The *E. coli* uvr-23 gene (also designated uvrY) is likely a member of a class of bacterial transcriptional activators, although no known function has yet been assigned to it in *E. coli*. A DNA fragment containing the uvr-23 gene was obtained by amplifying by the polymerase chain reaction (Mullis and Faloona, Methods in Enzymology 155:335–350 (1987)) a ca. 1.1 kb portion of the widely available *E. coli* K12 strain AB1157 genome. Primers for the polymerase chain reaction were prepared based upon the published sequence of uvr-23 (Sharma et al., Nucleic Acids Res. 14:2301–2318 (1986)). Two PCR primer oligonucleotides, 5'-GGCGGAGTATACCATAAG-3' and 5'-ATAAGCTTACCACCAGCATCGTAC-3' (SEQ ID NO's: 6 and 7, respectively) were used in the amplification of the ca. 1.1 kb DNA fragment at a concentration of 1 uM each in a 50 ul reaction mix containing, in reaction buffer supplied by the PCR kit manufacturer (Perkin Elmer Cetus), the four deoxyribonucleotides (dATP, dCTP, dGTP, and dTTP; 200 uM with respect to each), approximately 100 ng of *E. coli* K12 strain AB1157 genomic DNA, and 1 unit of Taq DNA polymerase. Typical amplification cycle times and temperatures were 94 C. for 1 min, followed by 45 C. for 1 min, followed by 72 C. for 1 min (30 cycles total). Amplified DNA fragments were digested with the restriction endonuclease HindIII, ligated with HindIII-digested pLAFR3, a broad-host-range plasmid capable of replication in Pseudomonas (Staskawicz et al., *J. Bacteriol.* 169:5789–5794 (1987)), and used to transform *E. coli*.

its native promoter, from a vector promoter, or from a heterologous promoter operatively joined to the ORF 5 coding region. Smaller DNA fragments are prepared from a template consisting of the cloned 2 kb XhoI fragment essentially by the procedure described for isolating the uvr-23 gene from *E. coli* in Example 5. Pairs of oligonucleotide piers are prepared for use in polymerase chain reaction amplification reactions. A common palmer annealing to the template downstream of ORF 5 is present in each primer pair, while the remaining primer of each pair anneals to a sequence at a different distance upstream of ORF 5. DNA fragments from amplification reactions are cloned in a broad-host-range plasmid such as pLAFR3 for introduction into *P. fluorescens*. *P. fluorescens* transconjugants are tested for activation of latent gene activities by assaying production of chitinase, cyanide, and pyrrolnitrin. The smallest fragment activating latent genes is identified.

Example 16

Formulations of antifungal compositions employing liquid compositions of transformed *P. fluorescens* bacteria which produce antibiotic substance inhibitory to the growth of *R. solani* as the active ingredient. In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethlene glycol ether | 5% | — | — |

-continued

| 1. Emulsifiable concentrates: | a | b | c |
|---|---|---|---|
| (36 moles of ethylene oxide) Tributylphenol polyethylene glycol ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate | — | — | 94% | — |

(boiling range 160–190°)

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgite | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 17

Formulation of antifungal compositions employing solid compositions of transformed *P. fluorescens* bacteria which produce antibiotic substance inhibitory to the growth of *R. solani* as the active ingredient.

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenyl polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

Example 18

Isolation of Further Pleiotropic Mutants

The transposon TnCIB116 is introduced into strain 915 by conjugation (Lain et al. (1990) Plant Soil 129:11–18). A collection of transposon insertion mutants of strain 915 is obtained and screened for the loss of pyrrolnitrin and chitinase production as described in Example 4. After screening 10,000 transposon mutants, seven pleiotropic mutants which no longer produce pyrrolnitrin, chitinase, or cyanide were obtained.

Example 19

Two Genetic Regions are Required for Gene Activation in Strain 915

The seven pleiotropic mutants fall into two genetic classes. pCIB 137 restored two of the seven transposon-induced mutants as well as mutant 2-1, to wildtype phenotype, suggesting that the genetic defects in these mutants were in ORF 5. Five mutants are not restored, indicating that at least one other genetic locus is required for gene activation in strain 915. A total gene library of strain 915 was introduced into these mutants by conjugation and transconjugants which has regained wildtype morphology were obtained. These transconjugants also produce pyrrolnitrin, chitinase, and cyanide. The restoring clones were isolated from these transconjugants. Restriction analysis indicates that the clones form an overlapping family of genetic fragments. The clones tested restored all five mutants of the second class to wildtype phenotype and had no effect on the two mutants of the first class. These clones define a second genetic region required for gene activation in strain 915. The smallest clone in the family, pCIB146, is analyzed further.

Example 20

Functional Analysis of the Second Genetic Region

Figure 4:
FIG. 4: This figure shows the ability of DNA subfragments derived from the clone pCIB 146 of *Pseudomonas fluorescens* strain 915 to complement the mutant CGP 21.

The done in pCIB146 was flanked by EcoRI sites (FIG. 4). There is one internal EcoRI site in the done. The two EcoRI subclones were obtained and tested for restoring ability. Neither one was able to restore mutant CGP 21, one of the five class II mutants, to wildtype phenotype, indicating that the internal EcoRI site defines a site critical to the functioning of the second genetic locus. There are two internal BamHI fragments in the clone. When these internal fragments were removed (pCIB191), the restoring ability was not affected. Finally, a 6 kb subclone containing only the region from the internal HindIII site to the leftmost internal BamHI site (pCIB168) retained restoring ability. Two clones were deposited which were able to complement the mutant: pCIB146 (about 25 kb) and pCIB168 (about 6 kb). pCIB146 was deposited with the NRRL on Jul. 29, 1993, and assigned accession number NRRL B-21118. pCIB168 was deposited with the NRRL on Jul. 29, 1993, and assigned accession number NRRL B-21117.

Example 21

The Second Genetic Region Contains a Gene Homologous to lemA

DNA sequences surrounding the internal EcoRI site in pCIB146 were obtained. Comparison against sequences contained in the Genbank database revealed significant homology with the lemA gene of *Pseudomonas syringae* pv. *syringae* strain B728a (Hrabak and Willis, 1992), a gene in the sensor family of two-component regulatory systems. See Table 6.

TABLE 6

Comparison of pCIB168 with the published lemA sequence by Hrabak et al. (1992) J. Bacteriol. 174:3011–3020

| lemA sequence coding start GTG = 788 | homology |
|---|---|
| 788–1063 | 72% |
| 1101–1886 | 77% |
| 1616–1886 | 87% |
| 2182–2308 | 78% |
| 2528–2843 | 72% |

Example 22

Introduction of the lemA Gene into Pseudomonas Strains for the Restoration of Biocontrol Functions Clone pCIB146 is introduced into mutant Pseudomonas strains which lack biocontrol functions due to an absence of the lemA gene. pCIB146 is introduced into Pseudomonas strains from *E. coli* by conjugation and is found to restore biocontrol functions, including chitinase, gelatinase, pyrrolnitrin and cyanide production.

Clone pCIB146 is also introduced into Pseudomonas strains which have no apparent defect in either the native lemA or gafA genes. An enhancement of biocontrol function, including production of chitinase, gelatinase, pyrrolnitrin and cyanide is found in the transformed strains by virtue of the increased lemA production in these strains overcoming a limitation in the capacity to phosphorylate the gafA protein.

The lemA gene is also introduced into Pseudomonas strains into which the gafA gene has already been introduced by the procedure described in Example 13. In this case the lemA gene is introduced on a plasmid which utilizes an origin of replication different to pLAFR3 to enable both gene constructions to be compatible in Pseudomonas. An enhancement of biocontrol function, including production of chitinase, gelatinase, pyrrolnitrin and cyanide is found in the strains expressing both transgenes by virtue of the increased lemA production in these strains overcoming a limitation in the capacity to phosphorylate the gafA protein, which in turn arises by virtue of the increased abundance of gafA in the pseudomonad cells.

In any of the experimental approaches described above the lemA gene could be expressed behind a heterologous promoter, instead of from its own promoter. Such a promoter would be required to be expressible in Pseudomonas cells and may be expressed either constitutively or in an inducible fashion.

Example 23

Modification of the lemA Gene to Increase its Kinase Activity on gafA

By corollary with other sensor components it is assumed that lemA functions by interaction of the amino-terminal part of the protein with an unknown signal, autophosphorylation of a histidine located towards the carboxyterminus of the protein, which thus allows the phosphorylation of the gafA protein. The kinase activity on gafA is increased using two experimental approaches.

First, the amino acid environment flanking the histidine autophosphorylation target is modified using PCR and cloning techniques well known in the art. Introduction of the modified lemA gene into Pseudomonas is achieved using a gene replacement technique (see example 9), and the Pseudomonas strains thus modified are assessed against nonmodified strains for chitinase, gelatinase, pyrrolnitrin, and cyanide production. Constructions which have a modified amino acid environment adjacent to the target histidine which render the histidine a better target for autophosphorylation also phosphorylate gafA more efficiently and thus produce elevated levels of chitinase, gelatinase, pyrrolnitrin and cyanide.

Second, the amino-terminal sensor part of the lemA gene is modified by deletion/substitution of amino acids using PCR and cloning techniques well known in the art. A series of modified constructions thus prepared are introduced into Pseudomonas strains using gene replacement techniques (see example 9), and the Pseudomonas strains thus modified are assessed against non-modified strains for chitinase, gelatinase, pyrrolnitrin, and cyanide production. Constructions which have a modified sensor domain are able to autophosphorylate the target histidine without the necessary interaction of the signal and may therefore phosphorylate gafA more efficiently and thus produce elevated levels of chitinase, gelatinase, pyrrolnitrin and cyanide.

Example 24

Modification of the gafA Gene to Increase the Efficiency of Phosphorylation of the Protein The amino acid environment flanking the presumed receiver domain of the gafA protein (around residue 54) is modified using PCR and cloning techniques. A series of modified constructions thus prepared are introduced into Pseudomonas strains using gene replacement techniques (see example 8b), and the Pseudomonas strains thus modified are assessed against non-modified strains for chitinase, gelatinase, pyrrolnitrin, and cyanide production. Constructions which have a modified receiver domain and which are more readily phosphorylated produce elevated levels of chitinase, gelatinase, pyrrolnitrin and cyanide.

Example 25

Pseudomonas Strains Carrying Improved lemA and gacA Genes lemA and gafA modifications described in Examples 19 and 20 which when introduced into Pseudomonas cause a phenotype of elevated production of chitinase, gelatinase, pyrrolnitrin and cyanide are combined into the same Pseudomonas strain by remodifying the improved lemA-carrying strain by repeating the gene replacement experiment with the improved gafA construction.

Example 26

Modification of gafA to Render the Protein Phosphorylation Independent

The gafA gene is modified so as to render the gafA protein phosphorylation independent. Since phosphorylation of the activator component of bacterial two-component regulatory systems leads to a conformational change in the DNA-binding domain of the activator, any specific amino acid substitutions, insertions, or deletions which lead to an equivalent conformational change render the activator phosphorylationindependent. The use of a phosphorylation-independent version of gafA in the activation of latent genes in bacterial strains removes the requirement that a strain contain an active version of LemA or an equivalent kinase.

The amino acid environment within the N-terminal half of gafA is modified using PCR and cloning techniques well known in the art. Such mutagenized versions of the gafA gene are cloned into broad-host-range plasmids and introduced into a lemA- mutant derivative of strain 915. Since introduction of the unaltered version of gafA into the lemA-mutant fails to restore synthesis of chitinase, pyrrolnitrin, cyanide, and gelatinase (see example 15), any altered versions of the GafA protein which do restore some level of synthesis of these compounds in the lemA-strain are locked into a constitutively active conformation (i.e. phosphorylationindependent).

Example 27

Cloning Antipathogenic Biosynthetic Genes by Exploiting Regulators which Control the Expression of the Biosynthetic Genes Regulators such as gafA, lemA and rpoS may be used to clone biosynthetic genes whose expression they control in the following manner. A library of transposon insertion mutants is created in a strain of microorganism which lacks the regulator or has had the regulator gene disabled by conventional gene disruption techniques. The insertion transposon used carries a promoter-less reporter gene (e.g. lacZ). Once the insertion library has been made, a functional copy of the regulator gene is transferred to the library of cells (e.g. by conjugation or electroporation) and the plated cells are selected for expression of the reporter gene. Cells are assayed before and after transfer of the regulator gene. Colonies which express the reporter gene only in the presence of the regulator gene are insertions adjacent to the promoter of genes regulated by the regulator. Assuming the regulator is specific in its regulation for APS-biosynthetic genes, then the genes tagged by this procedure will be APS-biosynthetic genes. These genes can then be cloned and further characterized using standard techniques well known in the art.

Example 28

Use of the gafA Regulator Gene for the Cloning of Pyrrolnitrin Biosynthetic Genes from Pseudomonas Pyrrolnitrin is an phenylpyrole compound produced by various strains of Pseudomonas fluorescens. P. fluorescens strains which produce pyrrolnitrin are effective biocontrol strains against Rhizoctonia and Pythium fungal pathogens (WO 94/01561). The biosynthesis of pyrrolnitrin is postulated to start from tryptophan (Chang et al., J. Antibiotics 34: 555–566 (1981)).

The gene cluster encoding pyrrolnitrin biosynthetic enzymes was isolated using the basic principle described in example 27 above. The regulator gene used in this isolation procedure was the gafA gene from Pseudomonas fluorescens and is known to be part of a two-component regulatory system controlling certain biocontrol genes in Pseudomonas. The gafA gene is described in detail in pending application 08/087,636 which is hereby incorporated by reference in its entirety and in the published application WO 94/01561. gafA is further described in Gaffney et al. (Mol. Plant Microbe Int. 7: 455–463 (1994)); also hereby incorporated in its entirety by reference) where it is referred to as "ORF5". The gafA gene has been shown to regulate pyrrolnitrin biosynthesis, chitinase, gelatinase and cyanide production. Strains which lack the gafA gene or which express the gene at low levels (and in consequence gafA-regulated genes also at low levels) are suitable for use in this isolation technique.

The transfer of the gafA gene from strain 915 to closely related non-pyrrolnitrin producing wild-type strains of *Pseudomonas fluorescens* results in the ability of these strains to produce pyrrolnitrin. (Gaffney et al., Mol. Plant Microbe Int. 7: 455–463 (1994)); see also Hill et al. Applied And Environmental Microbiology 60 78–85 (1994)). This indicates that these closely related strains have the structural genes needed for pyrrolnitrin biosynthesis but are unable to produce the compound without activation from the gafA gene. One such closely related strain, strain 914, was used for the identification of the pyrrolnitrin biosynthesis genes. The transposon TnCIB116 (Lain, New Directions in Biological Control: Alternatives for Suppressing Agricultural Pests and Diseases, pp 767–778, Alan R. Liss, Inc. (1990)) was used to mutagenize strain 914. This transposon, a Tn5 derivative, encodes kanamycin resistance and contains a promoterless lacZ reporter gene near one end. The transposon was introduced into strain 914 by conjugation, using the plasmid vector pCIB116 (Lain, New Directions in Biological Control: Alternatives for Suppressing Agricultural Pests and Diseases, pp 767–778, Alan R. Liss, Inc. (1990)) which can be mobilized into strain 914, but cannot replicate in that organism. Most, if not all, of the kanamycin resistant transconjugants were therefore the result of transposition of TnCIB116 into different sites in the strain 914 genome.

When the transposon integrates into the bacterial chromosome behind an active promoter the lacZ reporter gene is activated. Such gene activation can be monitored visually by using the substrate X-gal, which releases an insoluble blue product upon cleavage by the lacZ gene product. Kanamycin resistant transconjugants were collected and arrayed on master plates which were then replica plated onto lawns of *E. coli* strain S17-1 (Simon et al, Bio/techonology 1:784–791 (1983)) transformed with a plasmid carrying the wide host range RK2 origin of replication, a gene for tetracycline selection and the gafA gene. *E. coli* strain S 17-1 contains chromosomally integrated tra genes for conjugal transfer of plasmids. Thus, replica plating of insertion transposon mutants onto a lawn of the S17-1/gafA *E. coli* results in the transfer to the insertion transposon mutants of the gafA-carrying plasmid and enables the activity of the lacZ gene to be assayed in the presence of the gafA regulator (expression of the host gafA is insufficient to cause lacZ expression, and introduction of gafA on a multicopy plasmid is more effective). Insertion mutants which had a "blue" phenotype (i.e. lacZ activity) only in the presence of gafA were identified. In these mutants, the transposon had integrated within genes whose expression were regulated by gafA.

The ability to produce cyanide, chitinase, and pyrrolnitrin are activities known to be regulated by gafA (Gaffney et al., Mol. Plant Microbe Int. 7: 455–463 (1994). The mutants described above (with introduced gafA) were assayed for their ability to produce cyanide, chitinase, and pyrrolnitrin as described in Galley et al., Mol. Plant Microbe Int. 7: 455–463 (1994)). One mutant did not produce pyrrolnitrin but did produce cyanide and chitinase, indicating that the transposon had inserted in a genetic region involved only in pyrrolnitrin biosynthesis. DNA sequences flanking one end of the transposon were cloned by digesting chromosomal DNA isolated from the selected insertion mutant with XhoI, ligating the fragments derived from this digestion into the XhoI site of pSP72 (Promega, cat. #P2191) and selecting the *E. coli* transformed with the products of this ligation on kanamycin. The unique XhoI site within the transposon cleaves beyond the gene for kanamycin resistance and enabled the flanking region derived from the parent STRAIN 914 strain to be concurrently isolated on the same XhoI fragment. In fact the XhoI site of the flanking sequence was found to be located approximately 1 kb away from the end on the transposon.

A subfragment of the cloned XhoI fragment derived exclusively from the ~1 kb flanking sequence was then used to isolate the native (i.e. non-disrupted) gene region from a cosmid library of strain 915. The cosmid library was made from partially Sau3A digested strain 915 DNA, size selected for fragments of between 30 and 40 kb and cloned into the unique BamHI site of the cosmid vector pCIB119 which is a derivative of c2XB (Bates & Swift, Gene 26: 137–146 (1983)) and pRK290 (Ditta et al. Proc. Natl. Acad. Sci. USA 77: 7247–7351 (1980)). pCIB119 is a double-cos site cosmid vector which has the wide host range RK2 origin of replication and can therefore replicate in Pseudomonas as well as *E. coli*. Several clones were isolated from the strain 915 cosmid clone library using the ~1 kb flanking sequence as a hybridization probe. Of these one clone was found to restore pyrrolnitrin production to the transposon insertion mutant which had lost its ability to produce pyrrolnitrin. This clone had an insertion of ~32 kb and was designated pCIB169.

Example 29

Isolation of Genes Encoding Resorcinol

Two transposon-insertion mutants have been isolated which lack the ability to produce the antipathogenic substance 2-hexyl-5-propyl-resorcinol which is a further substance known to be under the global regulation of the gafA gene in *Pseudomonas fluorescens* (WO 94/01561). The insertion transposon TnCIB116 was used to generate libraries of mutants in strain 915 and a gafA⁻ derivative of strain 915 (BL1826). The former was screened for changes in fungal inhibition in vitro; the latter was screened for genes regulated by gafA after introduction of gafA on a plasmid (see Section C). Selected mutants were characterized by HPLC to assay for production of known compounds such as pyrrolnitrin and 2-hexyl-5-propyl-resorcinol. The HPLC assay enabled a comparison of the novel mutants to the wild-type parental strain. In each case, the HPLC peak corresponding to 2-hexyl-5-propyl-resorcinol was missing in the mutant. The mutant derived from strain 915 is designated BL1846. The mutant derived from BL1826 is designated BL1911.

The resorcinol biosynthetic genes can be cloned from the above-identified mutants in the following manner. Genomic DNA is prepared from the mutants, and clones containing the transposon insertion and adjacent Pseudomonas sequence are obtained by selecting for kanamycin resistant clones (kanamycin resistance is encoded by the transposon). The cloned Pseudomonas sequence is then used as a probe to identify the native sequences from a genomic library of *P. fluorescens* strain 915. The cloned native genes are likely to represent resorcinol biosynthetic genes.

Example 30

Identification and Cloning of the rpoS Gene Encoding the Alternate Sigma Factor rpoS (sigma-38) from *Pseudomonas fluorescens* Strain 915

In *Escherichia coli*, it has been demonstrated that an alternate sigma factor designated rpoS is required for the transcription of a large set of genes which are preferentially expressed during stationary phase conditions (i.e. conditions of nutrient stress) (Siegele and Kolter, J. Bacteriol. 174:345–348 (1992); Hengge-Aronis, Cell 72:165–168 (1993)). Antifungal factors involved in Pseudomonas biocontrol efficacy are actively expressed during stationary phase, creating the possibility that an rpoS homologue might exist in Pseudomonas. To investigate this possibility, an internal portion of the *E. coli* rpoS gene was obtained for use as a hybridization probe by designing polymerase chain reaction primers based on the published sequence of the *E. coli* rpoS gene (Mulvey and Loewen, Nucleic Acids Res. 17:9979–9991 (1989)) and altered to each contain a HindIII restriction site for subsequent cloning purposes. Two PCR palmer oligonucleotides, 5'-GGTCAAGCTTATGGGACAA-3' and 5'-GAGAAGCTTGCGTCTGGTGG-3' were used at a concentration of 1 uM each in a 50 ul reaction mix containing, in reaction buffer supplied by the PCR kit manufacturer (Perkin Elmer Cetus), the four deoxyribonucleotides (dATP, dCTP, dGTP, and dTTP; 200 uM with respect to each), approximately 100 ng of *E. coli* K12 strain AB1157 genomic DNA, and 1 unit of Taq DNA polymerase. Typical amplification cycle times and temperatures were 94 C. for 1 min, followed by 45 C. for 1 min, followed by 72 C. for 1 min (30 cycles total). These conditions resulted in the amplification of a ca. 265 base pair DNA fragment which was digested with HindIII and cloned into the HindIII site of pBluescript SK II+ (Stratagene). DNA sequence analysis of the ca. 265 base pair fragment confirmed that the sequence was an internal portion of the *E. coli* rpoS gene. The recombinant plasmid containing the ca. 265 base pair fragment was labeled by incorporating biotinylated dUTP in a random priming reaction as described by the manufacturer of the Flash Prime-IT II labeling and detection system (Stratagene, La Jolla, Calif.). The labeled plasmid was used as a hybridization probe against a preparation of genomic DNA isolated from *Pseudomonas fluorescens* strain 915 which had been digested with EcoRI, electrophoresed through a 0.7% agarose gel, and transferred by capillary blotting to a nylon membrane. A single hybridization band was observed, corresponding to a genomic EcoRI fragment of approximately 9 kb. Plasmid DNA preparations were prepared from pools consisting of 60 colonies each obtained from a cosmid library of *P. fluorescens* strain 915 DNA, digested with EcoRI, electrophoresed through a 0.7% agarose gel, and transferred to a I5 nylon membrane. The rpoS gene probe hybridized with a ca. 7 kb EcoRI fragment present from one such pooled preparation. This fragment likely represented a portion of the 9 kb genomic fragment which had previously hybridized, with one EcoRI site belonging to the cosmid vector. The 7 kb EcoRI fragment was subcloned from the cosmid vector into the EcoRI site of pBluescript SK II+. This plasmid was designated pCIB3360 and was deposited on Aug. 8, 1994, in an *E. coli* host with the NRRL (Agricultural Research Service Culture Collection, Peoria, Ill.) and assigned NRRL accession number B-21299. DNA sequence analysis revealed that the 7 kB EcoRI fragment did in fact have the cosmid vector EcoRI site as one endpoint and that this fragment contained the rpoS gene of *P. fluorescens* strain 915.

Example 31

Sequence of the *P. fluorescens* Strain 915 rpoS Gene

The DNA sequence of the *P. fluorescens* strain 915 rpoS gene and the deduced amino acid sequence of the RpoS sigma factor are provided in Sequence ID No. 8 and Sequence ID No. 9, respectively. The deduced amino add sequence is greater than 86% identical to that of the unpublished sequence of a *Pseudomonas aeruginosa* RpoS (Tanaka and Takahashi, Genbank accession #D26134, (1994)). It is also highly homologous to the *E. coli*, *Salmonella typhimurium*, and *Shigella flexneri* RpoS sigma factors (Mulvey and Loewen, Nucleic Acids Res. 17:9979–9991 (1989), GenBank accession #U05011, GenBank accession #U00119).

Example 32

Requirement of a Functional Copy of RpoS for the Expression of Biocontrol Factors and Secondary Metabolites A kanamycin resistance cartridge is cloned as a BamHI fragment from pUC4-KIXX (Pharmacia) into the rpoS gene of *P. fluorescens* strain 915. An EcoRI-BamHI fragment (derived from the 7 kb EcoRI fragment) containing the 5' half of rpoS is subcloned in pBluescript SK II+ adjacent to a BamHI-HindIII PCR amplification product consisting of sequences immediately downstream of rpoS. This subclone is digested with BamHI to allow insertion of the kanamycin resistance cartridge. This tagged defective version of rpoS is excised from pBluescript as an EcoRI fragment and cloned into the EcoRI site of the cloning vector pBR322. This pBR322 derivative is mobilized by conjugation into *P. fluorescens* strain 915. Since pBR322 cannot replicate in Pseudomonas, the majority of kanamycin resistant colonies result from recombination between rpoS or its flanking sequences and the homologous sequences in the *P. fluorescens* strain 915 chromosome. Double crossover events, in which the normal version of rpoS is replaced by the disrupted version, are detected as resulting in kanamycin resistant colonies which lack the pBR322 tetracycline resistance marker. Such events are confirmed by Southern hybridization. The constructed *P. fluorescens* rpoS mutants are tested for the production of antifungal factors and secondary metabolites such as pyrrolnitrin, chitinase, cyanide, and gelatinase and are found to be deficient or reduced in the production of these factors.

While the present invention has been described with reference to specific embodiments thereof; it will be appreciated that numerous variations, modifications, and embodiments are possible, and accordingly, all such variations, modifications and embodiments are to be regarded as being within the spirit and scope of the present invention.

What is claimed is:

1. An isolated gene activating element comprising a nucleotide sequence capable of inducing the expression of at least one gene in a Pseudomonad selected for transformation, wherein said gene is latent or expressed at low levels in said Pseudomonad, and wherein said nucleotide sequence is a *Pseudomonas fluorescens lemA* sequence comprised by the DNA fragment deposited as pCIB168.

2. A chimeric expression construct comprising the gene activating element of claim 1.

3. A plasmid vector comprising the gene activating element of claim 1.

4. A transgenic Pseudomonad into which the gene activating element of claim 1 has been introduced.

5. A method for activating expression in a Pseudomonas host of at least one gene that is latent or natively expressed at low levels, comprising introducing into said host at least one copy of the gene activating element of claim 1, wherein said gene activating element induces expression of said gene in said Pseudomonas host.

6. A method for rendering a Pseudomonas host effective against fungal pathogens, comprising introducing into said host at least one copy of the gene activating element of claim 1.

7. An isolated gene activating element comprising a nucleotide sequence capable of inducing the expression of at least one gene in a Pseudomonad selected for transformation, wherein said gene is latent or expressed at low levels in said Pseudomonad, and wherein said nucleotide sequence encodes the polypeptide encoded by a *Pseudomonas fluorescens lemA* sequence comprised by the DNA fragment deposited as pCIB168.

8. A chimeric expression construct comprising the gene activating element of claim 7.

9. A plasmid vector comprising the gene activating element of claim 7.

10. A transgenic Pseudomonad into which the gene activating element of claim 7 has been introduced.

11. A method for activating expression in a Pseudomonas host of at least one gene that is latent or natively expressed at low levels, comprising introducing into said host at least one copy of the gene activating element of claim 7, wherein said gene activating element induces expression of said gene in said Pseudomonas host.

12. A method for rendering a Pseudomonas host effective against fungal pathogens, comprising introducing into said host at least one copy of the gene activating element of claim 7.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
      ( A ) LENGTH: 642 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Pseudomonas fluorescens
      ( B ) STRAIN: CGA267356
      ( C ) INDIVIDUAL ISOLATE: ORF 5

( v i i ) IMMEDIATE SOURCE:
      ( B ) CLONE: pCIB137

( i x ) FEATURE:
      ( A ) NAME/KEY: CDS
      ( B ) LOCATION: 1..639
      ( D ) OTHER INFORMATION: /transl_except=(pos: 1 .. 3, aa: Met)

( x i ) SEQUENCE DESCRIPTION: SEQ ID NO:1:

```
TTG ATT AGG GTG CTA GTA GTC GAT GAC CAT GAT CTC GTT CGT ACA GGT     48
Met Ile Arg Val Leu Val Val Asp Asp His Asp Leu Val Arg Thr Gly
 1               5                  10                  15

ATT ACA CGA ATG CTG GCT GAC ATC GAT GGC CTG CAA GTG GTC GGC CAG     96
Ile Thr Arg Met Leu Ala Asp Ile Asp Gly Leu Gln Val Val Gly Gln
             20                  25                  30

GCC GAG TCA GGG GAG GAA TCC CTG CTC AAG GCC CGG GAG TTG AAA CCC    144
Ala Glu Ser Gly Glu Glu Ser Leu Leu Lys Ala Arg Glu Leu Lys Pro
         35                  40                  45

GAT GTG GTC CTC ATG GAC GTC AAG ATG CCC GGG ATC GGC GGT CTT GAA    192
Asp Val Val Leu Met Asp Val Lys Met Pro Gly Ile Gly Gly Leu Glu
     50                  55                  60

GCC ACG CGC AAA TTG TTG CGC AGT CAC CCG GAT ATC AAA GTC GTG GCC    240
Ala Thr Arg Lys Leu Leu Arg Ser His Pro Asp Ile Lys Val Val Ala
 65                  70                  75                  80

GTC ACC GTG TGT GAA GAA GAT CCG TTC CCG ACC CGC TTG CTG CAA GCC    288
Val Thr Val Cys Glu Glu Asp Pro Phe Pro Thr Arg Leu Leu Gln Ala
                 85                  90                  95

GGC GCG GCG GGT TAC CTG ACC AAG GGG GCG GGC CTC AAT GAA ATG GTG    336
Gly Ala Ala Gly Tyr Leu Thr Lys Gly Ala Gly Leu Asn Glu Met Val
            100                 105                 110

CAG GCC ATT CGC CTG GTG TTT GCC GGC CAG CGT TAC ATC AGC CCG CAA    384
Gln Ala Ile Arg Leu Val Phe Ala Gly Gln Arg Tyr Ile Ser Pro Gln
        115                 120                 125

ATT GCC CAG CAG TTG GTG TTC AAG TCA TTC CAG CCT TCC AGT GAT TCA    432
Ile Ala Gln Gln Leu Val Phe Lys Ser Phe Gln Pro Ser Ser Asp Ser
    130                 135                 140

CCG TTC GAT GCT TTG TCC GAG CGG GAA ATC CAG ATC GCG CTG ATG ATT    480
Pro Phe Asp Ala Leu Ser Glu Arg Glu Ile Gln Ile Ala Leu Met Ile
145                 150                 155                 160

GTC GGC TGC CAG AAA GTG CAG ATC ATC TCC GAC AAG CTG TGC CTG TCT    528
Val Gly Cys Gln Lys Val Gln Ile Ile Ser Asp Lys Leu Cys Leu Ser
                165                 170                 175
```

```
CCG  AAA  ACC  GTT  AAT  ACC  TAC  CGT  TAC  CGC  ATC  TTC  GAA  AAG  CTC  TCG     576
Pro  Lys  Thr  Val  Asn  Thr  Tyr  Arg  Tyr  Arg  Ile  Phe  Glu  Lys  Leu  Ser
               180                      185                      190

ATC  AGC  AGC  GAT  GTT  GAA  CTG  ACA  TTG  CTG  GCG  GTT  CGC  CAC  GGC  ATG     624
Ile  Ser  Ser  Asp  Val  Glu  Leu  Thr  Leu  Leu  Ala  Val  Arg  His  Gly  Met
               195                      200                      205

GTC  GAT  GCC  AGT  GCC  TGA                                                        642
Val  Asp  Ala  Ser  Ala
               210
```

( 2 ) INFORMATION FOR SEQ ID NO:2:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ile  Arg  Val  Leu  Val  Val  Asp  Asp  His  Asp  Leu  Val  Arg  Thr  Gly
 1                  5                   10                      15

Ile  Thr  Arg  Met  Leu  Ala  Asp  Ile  Asp  Gly  Leu  Gln  Val  Val  Gly  Gln
               20                  25                      30

Ala  Glu  Ser  Gly  Glu  Glu  Ser  Leu  Leu  Lys  Ala  Arg  Glu  Leu  Lys  Pro
          35                       40                 45

Asp  Val  Val  Leu  Met  Asp  Val  Lys  Met  Pro  Gly  Ile  Gly  Gly  Leu  Glu
     50                       55                      60

Ala  Thr  Arg  Lys  Leu  Leu  Arg  Ser  His  Pro  Asp  Ile  Lys  Val  Val  Ala
 65                       70                 75                           80

Val  Thr  Val  Cys  Glu  Glu  Asp  Pro  Phe  Pro  Thr  Arg  Leu  Leu  Gln  Ala
                    85                      90                            95

Gly  Ala  Ala  Gly  Tyr  Leu  Thr  Lys  Gly  Ala  Gly  Leu  Asn  Glu  Met  Val
               100                 105                      110

Gln  Ala  Ile  Arg  Leu  Val  Phe  Ala  Gly  Gln  Arg  Tyr  Ile  Ser  Pro  Gln
          115                 120                      125

Ile  Ala  Gln  Gln  Leu  Val  Phe  Lys  Ser  Phe  Gln  Pro  Ser  Ser  Asp  Ser
     130                      135                 140

Pro  Phe  Asp  Ala  Leu  Ser  Glu  Arg  Glu  Ile  Gln  Ile  Ala  Leu  Met  Ile
145                      150                 155                      160

Val  Gly  Cys  Gln  Lys  Val  Gln  Ile  Ile  Ser  Asp  Lys  Leu  Cys  Leu  Ser
                    165                      170                 175

Pro  Lys  Thr  Val  Asn  Thr  Tyr  Arg  Tyr  Arg  Ile  Phe  Glu  Lys  Leu  Ser
               180                      185                      190

Ile  Ser  Ser  Asp  Val  Glu  Leu  Thr  Leu  Leu  Ala  Val  Arg  His  Gly  Met
          195                      200                      205

Val  Asp  Ala  Ser  Ala
          210
```

( 2 ) INFORMATION FOR SEQ ID NO:3:

( i ) SEQUENCE CHARACTERISTICS:
        ( A ) LENGTH: 5559 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (iv) ANTI-SENSE: NO (vi) ORIGINAL SOURCE:
    (A) ORGANISM: Pseudomonas fluorescens
    (B) STRAIN: CGA267356
    (C) INDIVIDUAL ISOLATE: 5.6 kb EcoRI- HindIII restriction fragment (vii) IMMEDIATE SOURCE:
    (B) CLONE: pCIB137

(ix) FEATURE:
    (A) NAME/KEY: misc_feature
    (B) LOCATION: 210..1688
    (D) OTHER INFORMATION: /note="ORF 1, transcribed left to right"

(ix) FEATURE:
    (A) NAME/KEY: misc_feature
    (B) LOCATION: 1906..3633
    (D) OTHER INFORMATION: /note="ORF 2, transcribed left to right"

(ix) FEATURE:
    (A) NAME/KEY: misc_feature
    (B) LOCATION: 4616..4691
    (D) OTHER INFORMATION: /note="glyW, transcribed right to left"

(ix) FEATURE:
    (A) NAME/KEY: misc_feature
    (B) LOCATION: 4731..5318
    (D) OTHER INFORMATION: /note="ORF 3, transcribed right to left"

(xi) SEQUENCE DESCRIPTION: SEQ ID NO:3:

```
GAATTCGATG ACATGCCGCG CGCCGGCATC GACACGCAAA TGGTCGACCT GGTGCTGCCG      60
GTGGTCGAAA TGCCGCAGAA GCTGCTGGAG CTGTGGCGCA ACTCTCAGCT CATCACCCTG     120
CCGACCGCCA ACGATCCGCA AATCAAGGTC TCGGCGCCGG TGTCCAAACG CGATGCCGCG     180
GCGGCGAACA GCAGCTGCAA GACATCCTGA TGCTGTTGCG CACCGGCACC GGCCATGACT     240
TCAAGCATTA CAAGCGCGCC ACGGTGCTGC GGCGGATCGA GCGCCCGCTG CAGGTCACCG     300
CCCAGCCGGA CCTCGCCGCC TATCACGATT ACCTGCAGAT GCACCCTGAA GAAACCAAGG     360
CGCTGCTGGG CGACATGCTG ATCGGCGTGA CCAATTTCTT TCGCGACCGC GAGGCCTTCG     420
AAGCCCTGGA GCGCAATGTC ATTCCTGCCC TGGTGAAGTC CTTGCAGGAC AGCCAACCGC     480
ACCGTGAAGA CGTGCGCATC TGGTCCGCCG GCTGCTCCAC GGGTGAAGAG GCCTATAGCC     540
TGGCAATCGT CGCCAGCGAG CAGATGGCCC TGGAGGCCTG CAACGCCAAG CTGCAGGTAT     600
TCGCGACCGA TATCGACGAT CGTGCCATCG CCCAGGGACG CAAGGGGGTC TATCCCGAAG     660
CGATCGTTAC CGATGTGCCT CCGCAGCGCA TGCGCCAGTA CTTTTCCCGG GAAAACCAGC     720
ATTACCGGGT GCGCAAGGAG ATTCGCGAAA AGGTGCTGTT CGCCAAGCAC AGCCTGCTGG     780
CGGATCCGCC ATTTTCGCAG ATCGACTTGA TCGTCTGCCG TAACCTGCTG ATCTACCTGG     840
ACCGCGACGT GCAACGGGAG ATCCTGCAGA TGTTCCACTT CGCCCTGCGT CCTGGAGGCT     900
ACCTGTTCCT CGGTTCCTCC GAATCCGCGG ACGGCTGCCA GGATCTGTTC GTGCCGGTCG     960
ACAAGCGCAA CCGCATTTTC CGGGTACGGC CCAACTCGGC CACGGTTCGC CGCGCGCCCA    1020
CCATGCCGCG ACGGCGTACA TGCGCACCAT CGGCAGCCCC CACCCGTGG AAACCAAGTG     1080
TCTCGCGCAA AACCTCGTTC GCCGACATCC ACCTTCGCGC CCTGGAAAAG TGCGCGCCGC    1140
CGAGCATGAT CGTCGATGCC AACGCCGACA TCCTGCACAT GAGCGAAGGC GCCGGCCGGT    1200
TCCTGCGCTA TGTCGCGGGG GAAATCACCC GCAACCTGCT GACCCTGATC CAGCCCGAGC    1260
TGCGCCTTGA ACTGCGCACC ACGCTGTTCC AGGTGCAACA GTCCGGTGTT GCGGTGACCG    1320
```

| | | | | | |
|---|---|---|---|---|---|
| CCGCCGGGTG | CGCATCGAGC | GGGAAAAGAA | GCCTTGTTTC | ATCGACCTCA | CAGCCCGCCC | 1380
| CTTCAAGGAC | GAGGAAACCG | ACAACGAATA | TGTGCTGGTG | GTGTTCGAGG | AGACCGAGGC | 1440
| CGACCCACGG | GAGCTGCGCG | AGACCAGCGC | CAGCCAGACG | GAAAACCAGA | TGCTGGCCAA | 1500
| CCTCGAGCGG | GAGTTGCAGC | GGACCAAATT | GCACCTGCAG | GACACCATCG | AGCAATCGGA | 1560
| AGTCTCCAGC | GAGGAGCTCA | AGGCGTCGAA | CGAAGAAATG | CAGGCGCTCA | ATGAAGAGCT | 1620
| GCGCTCGGCC | ACCGAAGAGC | TGGAAACCAG | CAAGGAAGAG | TTGCAGTCGA | TCAATGAAGA | 1680
| GCTGCTGACG | GTCAATTACG | AGCTGAAAAC | CAAGGTCGAG | GAAACCGACA | AGATCAACGA | 1740
| CTACCTGACC | AACCTGATCG | CCTCCACCGA | CATCGCCACG | GTGTTCGTCG | ACCGCAACAT | 1800
| GCGCATCCGC | TGGTTCACCC | GCGCGCCAC | CGACATTTTC | AGCATGCTGC | CGGTGGACAC | 1860
| CGACGCTCAT | TACTGGACAT | CACCCACCGC | CTGAACTACC | CGGAAATGGC | CGAGGACGCC | 1920
| GCGACCGTGT | TCGAGTCGTT | GAGCATGATC | GAGCGTGAAG | TCAACAGCGA | CGATCAGCGC | 1980
| TGGTACATCG | CACGCCTGTT | GCCCTATCGC | TCCAGCGAAG | ACCATATCGA | CGGCACCGTG | 2040
| CTGACCTTCA | TCGATATCAC | CAAGCGCCGG | CTGGCCGAGG | AGGAACTGCG | CCTGGGCGAA | 2100
| GAACGCATGC | GCCTGGTCGC | CGAAAGCACC | CATGATTTCG | CCATCATCAT | CCTCGACAAC | 2160
| CAGGGCCTCA | TCACCGACTG | GAACACCGGG | GCGCAACTGA | TCTTCGGCTA | TACCAAGGAC | 2220
| GAAGTGCTGG | GCGCCTATTA | CGACCTGATT | TTCGCGCCTG | AGGACCGCGC | CGGCGGCGTG | 2280
| CCGGAAAGCG | AGCTGCTCAC | CGCCCGCGAA | CACGGCCGCA | GCGACGATGA | ACGCTGGCAT | 2340
| ATACGCAAGG | ACGGCGAGCG | CTTTTTCTGC | AGCGGCGAAG | TCACGCGGCT | CAAGGGTGAC | 2400
| AGCCTGCAAG | GCTACGTGAA | AATAGCCCGC | GACCTGACGG | GCCACAAACG | CATGCAGGAC | 2460
| GAGCAGAACC | AGAAGCTGAT | GGAGACCCAG | ACCCACAGCC | ACCTCAAGGA | TGAGTTTTTC | 2520
| GCGGTGATGT | CCCATGAACT | CAAGCATCCG | CTCAACCTGA | TCCAGCTCAA | CGCCGAGTTG | 2580
| CTGCGTCGCC | TGCCGACGAC | CAAGGCGGCC | GCCCTGCCC | TCAAGGCGGT | CAATACCATT | 2640
| TGCGAGGCTG | TCTCCAGCCA | GGCGCGGATC | ATCGACGACC | TGCTGGATGT | GCGGCGTTTG | 2700
| CGCACCGGCA | AGCTCAAGCT | GAAGAAACAG | CCGGTGGATC | TTGGCCGGAT | CCTGCAGGAC | 2760
| ATCCATACCG | TGGTGCTCAG | CGAAGGGCAT | CGCTGCCAGG | TGACGCTGCA | AGTGCCGTTG | 2820
| CCACCGCAAC | CGCCGTTAAT | GATCGATGCC | GATGCGACGC | GGCTGGAGCA | GGTGATCTGG | 2880
| AACCTGGTGA | ACAACGCCCT | GAAATTCACC | CCGGCCAATG | GCTTGGTCCA | GTTGATCGCC | 2940
| CAGCGGGTCG | AGGATAAGGC | GCACGTGGAT | GTCATCGACA | GCGGCGTGGG | CCTGGCCGAG | 3000
| GAAGACCAGA | ACAAGGTGTT | CGACCTTTTC | GGCCAGGCGG | CCAACCAGCA | CGGCACTCAT | 3060
| CAACGCGACG | GGCTGGGCAT | CGGCCTGTCA | CTGGTGCGCC | AGCTGGTGGA | AGCCCACGGC | 3120
| GGCTCGGTCA | GCGTGCAGTC | GAAGGGGCTG | GGCCAGGGAT | GCACCTTTAC | CGTGCTCTTG | 3180
| CCCCTGAGCC | ACCCCAACGA | CAGCGCTCCC | AAACAGCCCG | CGTCGCGGGG | TGTCGAACGC | 3240
| CTTGCCGGCA | TCAAGGTGCT | GCTGGTGGAC | GACTCGCGGG | AAGTCATGGA | AGTCCTGCAA | 3300
| CTGCTGCTGG | AGATGGAGGG | CGCGCAAGTC | GAGGCCTTCC | ACGACCCGCT | GCAGGCCTTG | 3360
| GGCAATGCCA | GGAACAACAG | TTACGACCTG | ATCATTTCAG | ACATCGGCAT | GCCGATTATG | 3420
| AACGGCTACG | AACTGATGCA | GAACCTGCGC | CAGATCGCTC | ACCTGCACCA | TACGCCAGCG | 3480
| ATTGCGCTGA | CCGGTTACGG | CGCCAGCAGC | GACCAGAAGA | AGTCCCAGCA | TGCGGGATTC | 3540
| GATCGGCATG | TGAGCAAACC | CGTGGCTCAG | GACCCGCTGA | TCGACCTGAT | CAGGGAGCTG | 3600
| TGCAGCCAGG | GCTTGCGCTC | GGCTGAGCAC | TGATGGTCTA | GACCCGGCGA | ACCCACCTCG | 3660
| TCGGCCTTGA | GCGCGGCGAG | CGCCATTGCC | TGCTGGGCAG | CTATTCACGC | TTGCGGATCG | 3720

```
TCGCGCCTGC GGGCCACCGC CTCTTTGATG GCTTGCTCAT AGGCGGCGTT GGCCTGGTCC    3780
TTGAGCTTGA GCCAATCGTC CCAATCGATC ACGCCGTTGC GCAGCAACTC CTCGGCCGCG    3840
CTTAACAGCG CCTGATGCCA GGCGTCCGGC GAGCCGGAAC GGTAGTCACG GTCTTCCAGC    3900
AGGCCTTGCC AGGCGTCCAG TTCCGGTGTC TTGCGTTCAT TGACCATGGC AGCCACGGCC    3960
TTTGTTCATT GCCGATAAAT CGGCGAGTGG GTGGTGGGTT TCTCGGATAT GCGCCCTGTC    4020
CTGCTCGAGA ACGGCCAGGC CGGGACATTG CTCAACGGTC AGCGACCGGA TGGAGCTCGA    4080
GCGGCATGCC ATCGACCAGC GTCAAGGTCA GGTTCTCGAT GGTGCCGGCG ATCCGGTCCT    4140
TGAATACCGG TTCGCCGTCC GGATCCAACT CATCGTAGAA AAAGCGCGTG CCTTCGAGCC    4200
AGCCAATGGT CGTTGCAGG TCCGGCCCCA GGTAATACTT GCCGTCAAGG AAAAACCCGG    4260
TAAAGGGCTC CACCCGCTCG CGATTCTCAA TGACATAACG TATTCCAGCG TGCATACCTG    4320
TCGATTTATC GAGCATGGCG TCGATCTCCC AGCAGATGAA TCCGGTAGAC CGCGTGGCTT    4380
TTTCACTGTT CCTTTTGATT GCCCGCCCGA CGCTGGCGAG CCTTGCTCGC GCGTCCTGGC    4440
CGCATTGCGC GGCGAATGGG CGACGTCGAA TCCGATCTGC AAGTGCCCAG CTAGCGGCCC    4500
GGCCACGGCA ATACGGGCTT CAGGTACGGC TTAGAAAGAA GAATGACGAT TGGCTCGACA    4560
TATTTTTTGG CGCAAAAAAA AATGGACCTC TTTTCAGAGG TCCATTTTTA ATATTTGGAG    4620
CGGGAAACGA GACTCGAACT CGCGACCCCG ACCTTGGCAA GGTCGTGCTC TACCAACTGA    4680
GCTATTCCCG CGTCTTGGTG GTGTGCATTT TATAGAAATT CGAAACTGCG TCAACCCCTT    4740
GATTCAAAAA GTTTTATTTC TTTTCTACCA TCGGTCTTCA GGTGCGGCCA GGCAGCGCGC    4800
AGGTACTGCA ACATCGACCA CAGGGTCAGC CCTCCGGCGA TCAGCAGGAA GGCATAACCC    4860
AGCAGCACCC AGAAGGTGAA GGCCGGCGGA TTGGCCAGCA GGATCACCAG CGCCAGCATC    4920
TGCGCGGCAG TTTTCCGATT TGCCCATGTT GGACACCGGC CACCTGGGCG CGTGCGNCCG    4980
AGCTCGGCCA TCCACTCGCG AAGGGCGGAC ACCACGATTT CACGCCCGAT GATCACCGCT    5040
GCCGGCAGGG TCAGCCACAG GTTGCCGTGC TCTTGCACCA GCAGCACCAG GGCCACCGCC    5100
ACCATCAACT TGTCGGCCAC CGGATCGAGG AAGGCCCCGA ACGGCGTGCT CTGCTCCAGA    5160
CGCCGCGCCA GGTAGCCATC AAGCCAGTCG GTGGCCGCGG CGAACGCAAA GACGGAACTG    5220
GCGGCCATGT AGCTCCAGTT GTAAGGCAGG TAAAACAGCA AATGAAGAT CGGGATGAGC    5280
AGAACGCGTA GAACGGTGAT CAGATTAGGG ATATTCATCG GCACAACTGG CTACGAGGTG    5340
AGTGGCAATC TACTCGGAAA AGACAGCAGA TGAGGTAGCA CGGCCATTCT ACGGGCTTCT    5400
GCCACAGCGT GTCTAACACT GTTCCAAGAC TTCGGGCCGC TCGAAAGAGC AACTTCAGAA    5460
GGTCTACACG CGCAAAATAA GACATTCAGT TCTTCTGTAA GTACCGTGTA GATCGGGATC    5520
TATCAGCGGT GCCCCGCCAA AAAGGAAGCC TTGAAGCTT                          5559
```

( 2 ) INFORMATION FOR SEQ ID NO:4:

( i ) SEQUENCE CHARACTERISTICS:
      ( A ) LENGTH: 983 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
      ( A ) ORGANISM: Pseudomonas fluorescens (B) STRAIN: CGA267356

(vii) IMMEDIATE SOURCE:
                (B) CLONE: pCIB137

(ix) FEATURE:
                (A) NAME/KEY: misc_feature
                (B) LOCATION: 23..51
                (D) OTHER INFORMATION: /note="sequence with promoter
                    homology"

(ix) FEATURE:
                (A) NAME/KEY: misc_feature
                (B) LOCATION: 99..740
                (D) OTHER INFORMATION: /note="ORF 5 structural gene"

(ix) FEATURE:
                (A) NAME/KEY: misc_feature
                (B) LOCATION: 743..983
                (D) OTHER INFORMATION: /note="5' end of ORF 4 (uvrC)"

(xi) SEQUENCE DESCRIPTION: SEQ ID NO:4:

| | | | | | |
|---|---|---|---|---|---|
| CCAAGTGCTT | TTTATATGGT | GTTTGTCATT | AGGTCAGCAC | GCTGCTTTTT | TGCTAAGGTG | 60
| TCCGGCAACC | TATAAGACCC | AAATCGCGAG | GTGTCTGCTT | GATTAGGGTG | CTAGTAGTCG | 120
| ATGACCATGA | TCTCGTTCGT | ACAGGTATTA | CACGAATGCT | GGCTGACATC | GATGGCCTGC | 180
| AAGTGGTCGG | CCAGGCCGAG | TCAGGGGAGG | AATCCCTGCT | CAAGGCCCGG | GAGTTGAAAC | 240
| CCGATGTGGT | CCTCATGGAC | GTCAAGATGC | CCGGGATCGG | CGGTCTTGAA | GCCACGCGCA | 300
| AATTGTTGCG | CAGTCACCCG | GATATCAAAG | TCGTGGCCGT | CACCGTGTGT | GAAGAAGATC | 360
| CGTTCCCGAC | CCGCTTGCTG | CAAGCCGGCG | CGGCGGGTTA | CCTGACCAAG | GGGCGGGCC | 420
| TCAATGAAAT | GGTGCAGGCC | ATTCGCCTGG | TGTTTGCCGG | CCAGCGTTAC | ATCAGCCCGC | 480
| AAATTGCCCA | GCAGTTGGTG | TTCAAGTCAT | TCCAGCCTTC | CAGTGATTCA | CCGTTCGATG | 540
| CTTTGTCCGA | GCGGGAAATC | CAGATCGCGC | TGATGATTGT | CGGCTGCCAG | AAAGTGCAGA | 600
| TCATCTCCGA | CAAGCTGTGC | CTGTCTCCGA | AAACCGTTAA | TACCTACCGT | TACCGCATCT | 660
| TCGAAAAGCT | CTCGATCAGC | AGCGATGTTG | AACTGACATT | GCTGGCGGTT | CGCCACGGCA | 720
| TGGTCGATGC | CAGTGCCTGA | CAATGACCGA | CCCGTTTGAT | CCCAGTGCTT | TTCTTTCCAC | 780
| CTGCAGTGGC | CGTCCTGGCG | TGTATCGCAT | GTTCGACAGC | GATACGCGTC | TGCTGTACGT | 840
| CGGTAAAGCC | AAGAACCTGA | AGAGCCGCCT | GGCCAGCTAC | TTTCGCAAGA | CCGGCCTGGC | 900
| GCCCAAGACC | GCTGCCCTGG | TGGGCGCAT | CGCAGATCGA | AACCACCATC | ACCGCCAACG | 960
| AGACCGAAGC | CCTGCTGCTC | GAG | | | | 983

(2) INFORMATION FOR SEQ ID NO:5:

(i) SEQUENCE CHARACTERISTICS:
                (A) LENGTH: 642 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

| | | | | | |
|---|---|---|---|---|---|
| TTGATTAGGG | TGCTAGTGGT | CGATGACCAT | GATCTCGTTC | GTACAGGTAT | TACCCGAATG | 60
| CTGGCTGACA | TCGATGGCCT | GCAAGTGGTC | GGTCAGGCCG | AGTCAGGGGA | GGAGTCCCTG | 120
| CTCAAGGCCC | GGGAGTTGAA | ACCCGATGTG | GTCCTCATGG | ACGTCAAGAT | GCCCGGGATC | 180

| | | | | | | |
|---|---|---|---|---|---|---|
| GGCGGTCTTG | AAGCCACGCG | CAAATTGTTG | CGCAGTCACC | CGGATATCAA | AGTCGTGGCC | 240 |
| GTCACCGTGT | GTGAAGAAGA | CCCGTTCCCG | ACCCGCTTGC | TGCAAGCCGG | TGCGGCGGGT | 300 |
| TACCTGACCA | AAGGTGCGGG | CCTCAATGAA | ATGGTGCAGG | CCATTCGCCT | GGTGTTTGCC | 360 |
| GGCCAGCGTT | ACATCAGCCC | GCAAATTGCC | CAGCAGTTGG | TGTTCAAGTC | ATTCCAGCCT | 420 |
| TCCAGTGATT | CACCGTTCGA | TGCTTTGTCC | GAGCGGGAAA | TCCAGATCGC | GCTGATGATT | 480 |
| GTCGGCTGCC | AGAAAGTGCA | GATCATCTCC | GACAAGCTGT | GCCTGTCTCC | GAAAACCGTT | 540 |
| AATATCTACC | GTTACCGCAT | CTTCGAAAAG | CTCTCGATCA | GCAGCGATGT | TGAACTGACA | 600 |
| TTGCTGGCGG | TTCGCCACGG | CATGGTCGAT | GCCAGTGCCT | GA | | 642 |

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGCGGAGTAT ACCATAAG                                                      18

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

ATAAGCTTAC CACCAGCATC GTAC                                          24

( 2 ) INFORMATION FOR SEQ ID NO:8:

( i ) SEQUENCE CHARACTERISTICS:
        ( A ) LENGTH: 1005 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( B ) STRAIN: single ( i x ) FEATURE:
        ( A ) NAME/KEY: CDS
        ( B ) LOCATION: 1..1005
        ( D ) OTHER INFORMATION: /product="alternate sigma factor
            RpoS"

( x i ) SEQUENCE DESCRIPTION: SEQ ID NO:8:

| | | | | | | | | | | | | | | | | |
|---|---|---|---|---|---|---|---|---|---|---|---|---|---|---|---|---|
| ATG | GCT | CTC | AGT | AAA | GAA | GTG | CCG | GAG | TTT | GAC | ATC | GAC | GAT | GAA | GTT | 48 |
| Met | Ala | Leu | Ser | Lys | Glu | Val | Pro | Glu | Phe | Asp | Ile | Asp | Asp | Glu | Val | |
| 1 | | | | 5 | | | | | 10 | | | | | 15 | | |
| CTC | CTT | ATG | GAG | ACG | GAT | ATC | GCC | GCT | GAT | TCG | ATG | TCG | AAT | GAG | GGA | 96 |
| Leu | Leu | Met | Glu | Thr | Asp | Ile | Ala | Ala | Asp | Ser | Met | Ser | Asn | Glu | Gly | |
| | | | 20 | | | | 25 | | | | | 30 | | | | |
| TCT | GCT | GTA | CCT | TCA | GTT | CGT | GCC | AAA | TCC | AAA | CAC | TCC | GCT | TCA | TTG | 144 |
| Ser | Ala | Val | Pro | Ser | Val | Arg | Ala | Lys | Ser | Lys | His | Ser | Ala | Ser | Leu | |
| | | 35 | | | | | 40 | | | | | 45 | | | | |
| AAA | CAA | CAT | AAA | TAC | ATT | GAT | TAC | ACG | CGG | GCG | CTC | GAC | GCG | ACG | CAG | 192 |
| Lys | Gln | His | Lys | Tyr | Ile | Asp | Tyr | Thr | Arg | Ala | Leu | Asp | Ala | Thr | Gln | |
| | 50 | | | | | 55 | | | | | 60 | | | | | |
| TTG | TAT | CTC | AAT | GAA | ATC | GGC | TTT | TCC | CCA | TTG | CTC | TCT | CCG | GAA | GAA | 240 |
| Leu | Tyr | Leu | Asn | Glu | Ile | Gly | Phe | Ser | Pro | Leu | Leu | Ser | Pro | Glu | Glu | |
| 65 | | | | | 70 | | | | | 75 | | | | | 80 | |
| GAA | GTT | CAT | TTT | GCG | CGT | CTT | TCA | CAA | AGT | GGT | GAT | CCG | GCC | GGG | CGC | 288 |
| Glu | Val | His | Phe | Ala | Arg | Leu | Ser | Gln | Ser | Gly | Asp | Pro | Ala | Gly | Arg | |
| | | | | 85 | | | | | 90 | | | | | 95 | | |
| AAG | CGC | ATG | ATT | GAA | AGC | AAC | CTG | CGT | CTG | GTG | GTG | AAA | ATC | ACC | CGA | 336 |
| Lys | Arg | Met | Ile | Glu | Ser | Asn | Leu | Arg | Leu | Val | Val | Lys | Ile | Thr | Arg | |
| | | | 100 | | | | | 105 | | | | | 110 | | | |
| CGC | TAT | GTC | AAT | CGC | GGG | CTT | TCA | CTG | CTG | GAC | CTC | ATC | GAA | GAG | GGC | 384 |
| Arg | Tyr | Val | Asn | Arg | Gly | Leu | Ser | Leu | Leu | Asp | Leu | Ile | Glu | Glu | Gly | |
| | | 115 | | | | | 120 | | | | | 125 | | | | |
| AAC | CTC | GGT | NTG | ATC | CGG | NCG | GTG | GAG | AAG | ATT | GAC | CCG | GAG | CGC | GGT | 432 |
| Asn | Leu | Gly | Xaa | Ile | Arg | Xaa | Val | Glu | Lys | Ile | Asp | Pro | Glu | Arg | Gly | |
| | 130 | | | | | 135 | | | | | 140 | | | | | |
| TTC | CGC | TTC | TCG | ACC | TAT | GCC | ACC | TGG | TGG | ATC | CGT | CAA | ACC | ATC | GAA | 480 |
| Phe | Arg | Phe | Ser | Thr | Tyr | Ala | Thr | Trp | Trp | Ile | Arg | Gln | Thr | Ile | Glu | |
| 145 | | | | | 150 | | | | | 155 | | | | | 160 | |
| CGG | NCA | ATC | ATG | AAC | CAG | ACC | CGG | ACT | ATC | CGN | CTG | CCG | ATT | CAT | GTG | 528 |
| Arg | Xaa | Ile | Met | Asn | Gln | Thr | Arg | Thr | Ile | Xaa | Leu | Pro | Ile | His | Val | |
| | | | | 165 | | | | | 170 | | | | | 175 | | |
| GTC | AAA | GAG | CTC | AAC | GTC | TAC | CTG | CGG | GCA | GCA | CGT | GAG | CTG | ACT | CAG | 576 |
| Val | Lys | Glu | Leu | Asn | Val | Tyr | Leu | Arg | Ala | Ala | Arg | Glu | Leu | Thr | Gln | |
| | | | 180 | | | | | 185 | | | | | 190 | | | |
| AAA | CTC | GAC | CAT | GAA | CCT | TCC | CCT | GNA | GAA | ATC | GCC | AAC | CTG | CTG | GAG | 624 |
| Lys | Leu | Asp | His | Glu | Pro | Ser | Pro | Xaa | Glu | Ile | Ala | Asn | Leu | Leu | Glu | |
| | | 195 | | | | | 200 | | | | | 205 | | | | |
| AAA | CCG | GTA | GGT | GAG | GTC | AAG | CGC | ATG | CTG | GGT | CTC | AAT | GAG | CGG | GTG | 672 |
| Lys | Pro | Val | Gly | Glu | Val | Lys | Arg | Met | Leu | Gly | Leu | Asn | Glu | Arg | Val | |
| | 210 | | | | | 215 | | | | | 220 | | | | | |
| TCT | TCA | GTC | GAC | GTC | TCG | CTG | GGT | CCG | GAT | TCG | GAT | AAA | ACC | CTG | CTG | 720 |
| Ser | Ser | Val | Asp | Val | Ser | Leu | Gly | Pro | Asp | Ser | Asp | Lys | Thr | Leu | Leu | |
| 225 | | | | | 230 | | | | | 235 | | | | | 240 | |
| GAC | ACC | CTC | ACC | GAC | GAT | CGC | CCA | ACC | GAT | CCG | TGC | GAG | CTG | CTG | CAG | 768 |
| Asp | Thr | Leu | Thr | Asp | Asp | Arg | Pro | Thr | Asp | Pro | Cys | Glu | Leu | Leu | Gln | |
| | | | | 245 | | | | | 250 | | | | | 255 | | |
| GAT | GAC | GAC | CTG | TCG | CAA | AGC | ATC | GAT | CAG | TGG | CTT | TCC | GAA | CTG | ACC | 816 |
| Asp | Asp | Asp | Leu | Ser | Gln | Ser | Ile | Asp | Gln | Trp | Leu | Ser | Glu | Leu | Thr | |
| | | | 260 | | | | | 265 | | | | | 270 | | | |
| GAC | AAG | CAG | CGT | GAA | GTA | GTG | GTT | CGC | CGC | TTC | GGC | TTG | CGC | GGC | CAT | 864 |
| Asp | Lys | Gln | Arg | Glu | Val | Val | Val | Arg | Arg | Phe | Gly | Leu | Arg | Gly | His | |
| | | 275 | | | | | 280 | | | | | 285 | | | | |
| GAA | AGC | AGC | ACC | CTG | GAA | GAT | GTG | GGC | CTG | GAG | ATC | GGT | CTT | ACC | CGA | 912 |
| Glu | Ser | Ser | Thr | Leu | Glu | Asp | Val | Gly | Leu | Glu | Ile | Gly | Leu | Thr | Arg | |
| | 290 | | | | | 295 | | | | | 300 | | | | | |
| GAG | CGG | GTA | CGC | CAG | ATC | CAG | GTC | GAA | GGT | CTC | AAG | CGC | CTG | CGC | GAG | 960 |
| Glu | Arg | Val | Arg | Gln | Ile | Gln | Val | Glu | Gly | Leu | Lys | Arg | Leu | Arg | Glu | |
| 305 | | | | | 310 | | | | | 315 | | | | | 320 | |

```
ATC CTC GAA AAG AAC GGC CTT TCC AGC GAG TCG CTG TTC CAG TAA          1005
Ile Leu Glu Lys Asn Gly Leu Ser Ser Glu Ser Leu Phe Gln  *
                325                 330                 335
```

( 2 ) INFORMATION FOR SEQ ID NO:9:

( i ) SEQUENCE CHARACTERISTICS:
        ( A ) LENGTH: 334 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Ala Leu Ser Lys Glu Val Pro Glu Phe Asp Ile Asp Asp Glu Val
 1               5                  10                  15

Leu Leu Met Glu Thr Asp Ile Ala Ala Asp Ser Met Ser Asn Glu Gly
             20                  25                  30

Ser Ala Val Pro Ser Val Arg Ala Lys Ser Lys His Ser Ala Ser Leu
         35                  40                  45

Lys Gln His Lys Tyr Ile Asp Tyr Thr Arg Ala Leu Asp Ala Thr Gln
     50                  55                  60

Leu Tyr Leu Asn Glu Ile Gly Phe Ser Pro Leu Leu Ser Pro Glu Glu
 65                  70                  75                  80

Glu Val His Phe Ala Arg Leu Ser Gln Ser Gly Asp Pro Ala Gly Arg
                 85                  90                  95

Lys Arg Met Ile Glu Ser Asn Leu Arg Leu Val Val Lys Ile Thr Arg
             100                 105                 110

Arg Tyr Val Asn Arg Gly Leu Ser Leu Leu Asp Leu Ile Glu Glu Gly
         115                 120                 125

Asn Leu Gly Xaa Ile Arg Xaa Val Glu Lys Ile Asp Pro Glu Arg Gly
     130                 135                 140

Phe Arg Phe Ser Thr Tyr Ala Thr Trp Trp Ile Arg Gln Thr Ile Glu
145                 150                 155                 160

Arg Xaa Ile Met Asn Gln Thr Arg Thr Ile Xaa Leu Pro Ile His Val
                 165                 170                 175

Val Lys Glu Leu Asn Val Tyr Leu Arg Ala Ala Arg Glu Leu Thr Gln
             180                 185                 190

Lys Leu Asp His Glu Pro Ser Pro Xaa Glu Ile Ala Asn Leu Leu Glu
         195                 200                 205

Lys Pro Val Gly Glu Val Lys Arg Met Leu Gly Leu Asn Glu Arg Val
     210                 215                 220

Ser Ser Val Asp Val Ser Leu Gly Pro Asp Ser Asp Lys Thr Leu Leu
225                 230                 235                 240

Asp Thr Leu Thr Asp Asp Arg Pro Thr Asp Pro Cys Glu Leu Leu Gln
                 245                 250                 255

Asp Asp Asp Leu Ser Gln Ser Ile Asp Gln Trp Leu Ser Glu Leu Thr
             260                 265                 270

Asp Lys Gln Arg Glu Val Val Val Arg Arg Phe Gly Leu Arg Gly His
         275                 280                 285

Glu Ser Ser Thr Leu Glu Asp Val Gly Leu Glu Ile Gly Leu Thr Arg
     290                 295                 300

Glu Arg Val Arg Gln Ile Gln Val Glu Gly Leu Lys Arg Leu Arg Glu
305                 310                 315                 320

Ile Leu Glu Lys Asn Gly Leu Ser Ser Glu Ser Leu Phe Gln
                 325                 330
```